(12) United States Patent
Torchilin et al.

(10) Patent No.: US 9,931,418 B2
(45) Date of Patent: Apr. 3, 2018

(54) COMPOSITIONS FOR THE DELIVERY OF RNA AND DRUGS INTO CELLS

(71) Applicant: Northeastern University, Boston, MA (US)

(72) Inventors: Vladimir Torchilin, Charlestown, MA (US); Swati Biswas, Boston, MA (US)

(73) Assignee: Northeastern University, Boston, MA (US)

( * ) Notice: Subject to any disclaimer, the term of this patent is extended or adjusted under 35 U.S.C. 154(b) by 253 days.

(21) Appl. No.: 14/420,143

(22) PCT Filed: Aug. 6, 2013

(86) PCT No.: PCT/US2013/053809
§ 371 (c)(1),
(2) Date: Feb. 6, 2015

(87) PCT Pub. No.: WO2014/025795
PCT Pub. Date: Feb. 13, 2014

(65) Prior Publication Data
US 2015/0216991 A1 Aug. 6, 2015

Related U.S. Application Data

(60) Provisional application No. 61/680,340, filed on Aug. 7, 2012.

(51) Int. Cl.
| | |
|---|---|
| *A61K 47/48* | (2006.01) |
| *C08G 73/02* | (2006.01) |
| *A61K 48/00* | (2006.01) |
| *A61K 31/704* | (2006.01) |
| *A61K 31/713* | (2006.01) |
| *A61K 31/785* | (2006.01) |
| *A61K 31/795* | (2006.01) |
| *C12N 15/113* | (2010.01) |
| *A61K 9/107* | (2006.01) |
| *C12N 15/11* | (2006.01) |
| *C08G 83/00* | (2006.01) |
| *A61K 47/59* | (2017.01) |
| *A61K 47/69* | (2017.01) |
| *C08G 81/00* | (2006.01) |

(52) U.S. Cl.
CPC .......... *A61K 47/488* (2013.01); *A61K 9/1075* (2013.01); *A61K 31/704* (2013.01); *A61K 31/713* (2013.01); *A61K 31/785* (2013.01); *A61K 31/795* (2013.01); *A61K 47/595* (2017.08); *A61K 47/6907* (2017.08); *A61K 48/00* (2013.01); *C08G 73/0206* (2013.01); *C08G 83/004* (2013.01); *C12N 15/111* (2013.01); *C12N 15/113* (2013.01); *C08G 81/00* (2013.01); *C12N 2310/14* (2013.01); *C12N 2320/32* (2013.01)

(58) Field of Classification Search
CPC ...... A61K 31/16; A61K 48/00; C08G 83/003; C08G 73/028; C08G 83/004; C08G 73/0206
See application file for complete search history.

(56) References Cited

U.S. PATENT DOCUMENTS

| | | | |
|---|---|---|---|
| 7,709,457 | B2 | 5/2010 | Esuvaranathan et al. |
| 2006/0216342 | A1 | 9/2006 | Torchilin et al. |

FOREIGN PATENT DOCUMENTS

| | | |
|---|---|---|
| WO | WO-2008/137470 | 11/2008 |
| WO | WO-2012/024396 | 2/2012 |

OTHER PUBLICATIONS

Mandeville et al "Probing the Binding of Cationic Lipids with Dendrimers", Biomacromolecules 2013, 14, 142-152, Published: Nov. 6, 2012).*
Kojima et al "Synthesis of Polyamidoamine Dendrimers Having Poly(ethylene glycol) Grafts and Their Ability to Encapsulate Anticancer Drugs", Bioconjugate Chem. 2000, 11, 910-917.in Nov. 2000.*
International Search Report & Written Opinion on PCT/US2013/053809 dated Jan. 3, 2014.
Koren et. al. Multifunctional PEGylated 2C5-Immunoliposomes Containing pH-sensitive Bonds and TAT Peptide for Enhanced Tumor Cell Internalization and Cytotoxicity in Journal of Controlled Release, Jun. 10, 2012 (Jun. 10, 2012), 160(2), 264-273. p. 5, para 4; p. 7, para 3; p. 8, para 4 to p. 9, para 1; p. 17, Figure 3C.
Takahashi, T., Kono, K., Itoh, T., Emi, N., and Takagishi, T., Synthesis of Novel Cationic Lipids Having Polyamidoamine Dendrons and Their Transfection Activity, Bioconjugate Chemistry, vol. 14, No. 4, pp. 764-773, Jul./Aug. 2003.

* cited by examiner

*Primary Examiner* — Gregory Listvoyb
(74) *Attorney, Agent, or Firm* — Posternak Blankstein & Lund LLP

(57) ABSTRACT

Provided is a co-polymer of formula A-L-D, or a pharmaceutically acceptable salt thereof, wherein A is a linear, branched or dendritic polyamine; D is a lipid; and L is a linker comprising a water soluble polymer; wherein L is connected to A at a first end through a first covalent bond and connected to D at a second end through a second covalent bond.

20 Claims, 15 Drawing Sheets

COMPOSITIONS FOR THE DELIVERY OF RNA AND DRUGS INTO CELLS

RELATED APPLICATION

This application is the U.S. 371 National Stage Application of PCT International Application No. PCT/US2013/53809, filed Aug. 6, 2013, which claims benefit of and priority to U.S. provisional patent application U.S. Ser. No. 61/680,340, filed Aug. 7, 2012, the entire contents of which are incorporated herein by reference in their entireties.

STATEMENT OF GOVERNMENT INTEREST

This invention was made with government support under R01 CA121838 and R01 CA128486 awarded by the National Institute of Health. The government has certain rights in the invention.

BACKGROUND

Small interfering RNA (siRNA) is a short, double-stranded nucleic acid molecule that can be used for post-transcriptional gene silencing. In theory, siRNA can be used to suppress the expression of e.g., cancer-related genes by silencing specific complementary mRNA associated with those genes and down-regulating expression of the associated gene products, e.g., proteins. It would be advantageous to co-administer siRNA, for the silencing of cancer related genes, with small molecule cancer drugs to more effectively treat cancer.

In practice, however, the therapeutic application of siRNA technology has been limited because siRNA is difficult to effectively deliver to the site of its action in a subject. Naked siRNA is water soluble, readily degraded by endogenous enzymes and generally too large and negatively charged to cross cell membranes by diffusion, a mechanism by which small molecule drugs generally enter cells.

Many small molecule drugs are also difficult to administer to a subject, but for different reasons. Many small molecule cancer drugs have poor aqueous solubility and, e.g., for intravenous (IV) administration, require large volumes of an aqueous vehicle. Alternatively, a more direct administration (e.g., subcutaneous delivery) of many small molecule cancer drugs can result in local toxicity and low levels of activity. Thus, there is a need for more efficient and effective delivery to subjects of both siRNA and small molecule chemotherapeutic agents.

SUMMARY

The present technology provides co-polymers, compositions comprising the same and related methods of use for the efficient delivery of siRNA, a small-molecule drug or both an siRNA and a small molecule drug, to disease-associated target cells or tissues. In some embodiments, the disease is cancer. Delivery of the siRNA, the small-molecule drug. or both the siRNA and small molecule drug, is facilitated by the disclosed co-polymer, which includes, in some embodiments, a linear, branched or dendritic polyamine. In some embodiments, the dendritic polyamine comprising co-polymer facilitates intracellular uptake of siRNA, the small-molecule drug, or both of these agents into target cells.

The siRNA species to be delivered will be determined by the disease state to be treated. As discussed in more detail below, tens of thousands of siRNA sequences directed to mRNAs are associated with a broad variety of disease states. Such siRNA sequences are known in the art and may be identified from public databases and/or purchased from commercial vendors. In some embodiments, the small-molecule drug to be delivered is a chemotherapeutic drug.

According to one aspect, a co-polymer of formula A-L-D, or a pharmaceutically acceptable salt thereof, is provided wherein A is a linear, branched or dendritic polyamine; D is a lipid; and L is a linker comprising a water soluble polymer; wherein L is connected to A at a first end through a first covalent bond and connected to D at a second end through a second covalent bond.

In some embodiments, provided is co-polymer of formula (I)

$$\text{A-B-C-D} \tag{I}$$

or a pharmaceutically acceptable salt thereof, wherein
A is a poly(amidoamine) dendrimer (PAMAM);
B is selected from the group consisting of a bond, —CO—, —COO—, —CONR$_5$—, —CH$_2$CH$_2$CO—, —CH$_2$CH$_2$COO—, —CH$_2$CH$_2$CONR$_5$—, —SO$_2$— and —SO$_2$NR$_5$—;
C is —(R$_4$O)$_n$—;
D is F, EF or E(F)$_2$;
E is selected from the group consisting of a bond, —COO—, —CONR$_5$—, —CH$_2$CH$_2$COO—, —CH$_2$CH$_2$CONR$_5$—, —SO$_2$NR$_5$—;

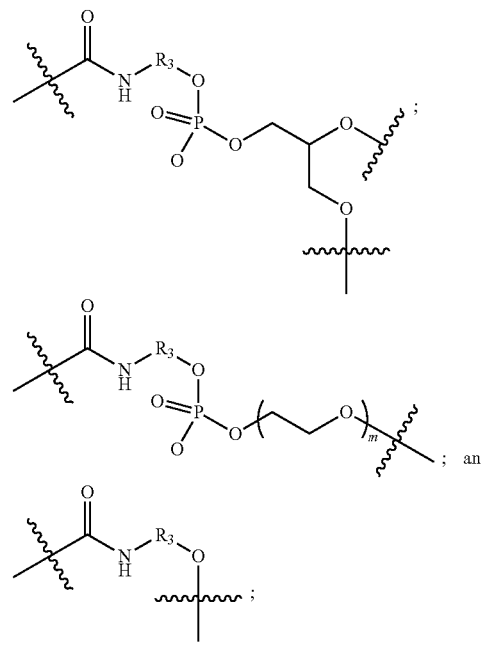

F is —CO—C$_6$-C$_{22}$-alkyl or —CO—C$_6$-C$_{22}$-alkenyl;
R$_3$ is C$_2$-C$_8$ alkylene, optionally substituted;
R$_4$ is C$_2$-C$_8$ alkylene, optionally substituted;
R$_5$ is hydrogen or C$_1$-C$_6$ alkyl, optionally substituted;
n is from 1 to 50; and
m is from 1 to 50.

In another aspect, a micellar composition is provided where the micellar composition includes any of the linear, branched or dendritic polyamine comprising co-polymers described herein. In some embodiments, the co-polymer is poly(ethylene glycol)-dioleoylphosphatidyl ethanolamine (PEG-DOPE) modified G(4)-PAMAM nanocarrier (i.e., G(4)-PAMAM-PEG-2K-DOPE).

In some embodiments, a "mixed" micellar composition is provided, comprising any one of the linear, branched or dendritic polyamine comprising co-polymers described herein, such as G(4)-PAMAM-PEG-2K-DOPE, and an "additional co-polymer" that generally lacks a linear, branched or dendritic polyamine moiety such as, for example, polyethylene glycol-phosphatidylethanolamine i.e., PEG-$_{5K}$-PE.

In some embodiments, the micellar compositions and mixed micellar compositions described herein are found to (i) have higher micellization efficiency with low critical micelle concentration (CMC) and higher drug loading, (ii) impart higher stability and protection of the condensed siRNA against enzymatic degradation, (iii) have enhanced cell penetration resulting in efficient transfection, and (iv) have lesser cytotoxicity due to PEGylation and less systemic immunogenicity.

In another aspect, a method for delivering siRNA and/or a chemotherapeutic drug into one or more cells of a subject is provided, where the method comprises administering to the subject an effective amount of a composition comprising any of the co-polymers described herein, siRNA and/or the chemotherapeutic drug.

In another aspect, a method for treating cancer in a subject is provided, where the method comprises administering to the subject an effective amount of a composition comprising any of the co-polymers described herein, siRNA and/or a chemotherapeutic drug.

In another aspect, a method is provided for treating cancer in a subject comprising administering to the subject an effective amount of any of the micellar compositions described herein.

In another aspect, a method is provided for delivering siRNA and a chemotherapeutic drug into one or more cells of a subject comprising administering to the subject an effective amount of any of the micellar compositions described herein.

BRIEF DESCRIPTION OF THE DRAWINGS

The foregoing and other objects, aspects, features and advantages of the disclosure will become more apparent and better understood by referring to the following description taken in conjunction with the accompanying non-limiting drawings.

Described, illustrated and tested herein are "mixed" dendrimers or micelles thereof, (MDM), modified dendrimers PAMAM G(4)-D-PEG$_{2K}$-DOPE or micelles thereof, (MD), and PAMAM G(4)-dendrimers (D). MDM, MD and D are referred to herein, individually and collectively, as "nanocarriers." The term "dendriplex" refers to a complex formed from any of the nanocarriers described herein and siRNA, and optionally a small-molecule drug. The term "micelle" is used according to its generally accepted meaning.

The "mixed" modified dendrimer-micelles (MDM) were prepared by mixing modified dendrimers PAMAM G(4)-D-PEG$_{2K}$-DOPE (MD), an exemplary "co-polymer," or micelles thereof, with PEG-5K-DOPE, an exemplary "additional co-polymer," at a molar ratio of about 1:1. MDM and MD were compared against PAMAM G(4)-dendrimers (D).

Figure 1:
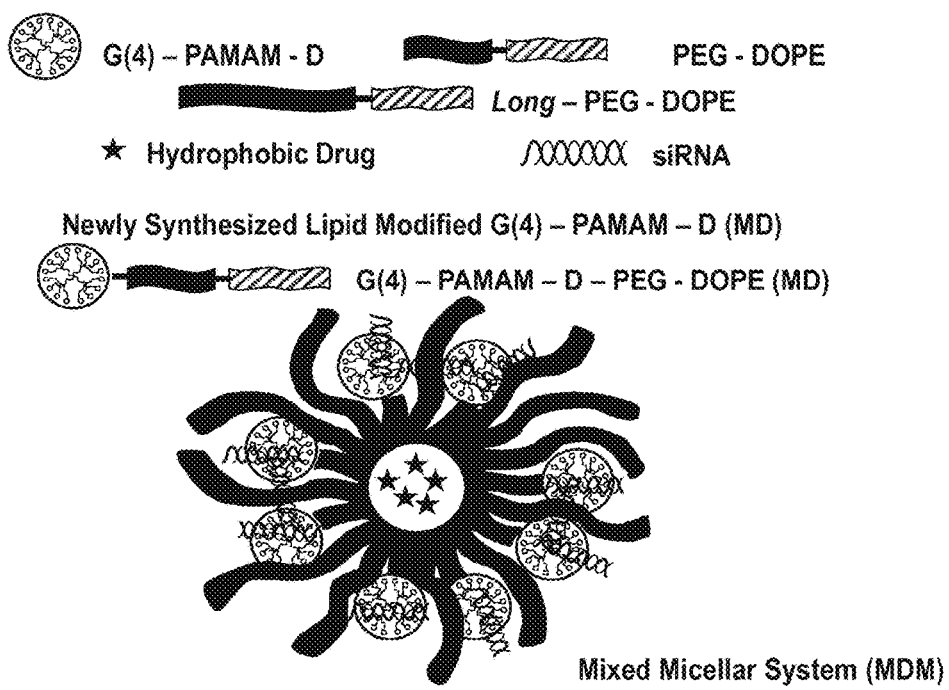

FIG. 1 illustrates the formation of "mixed" micelle system MDM made with G(4)-PAMAM-D-PEG-DOPE/PEG-DOPE.

Figure 2:
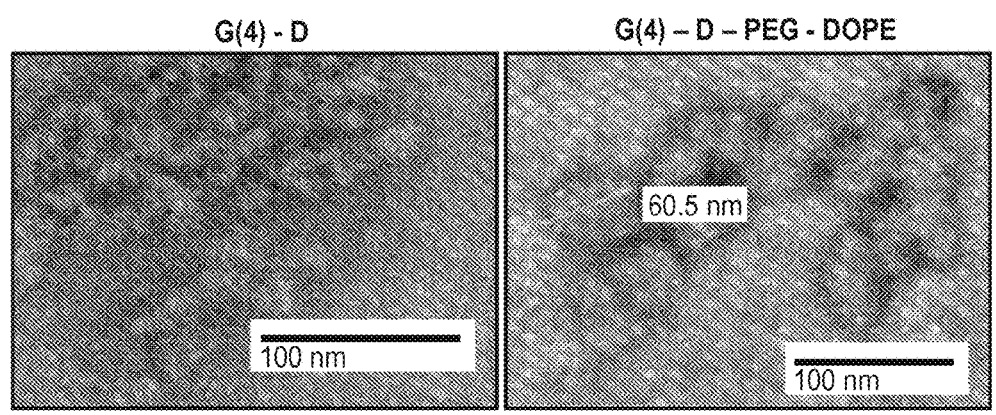

FIG. 2 shows a TEM image of G(4)-PAMAM-D and G(4)-D-PAMAM-PEG-DOPE.

FIG. 3 shows the binding ability of tested nanocarriers to siRNA. Different ratios of nitrogen in G(4)-D to phosphate in siRNA (N/P) of the nanocarriers were tested by gel retardation assay (A) and ethidium bromide exclusion assay (B) and (C). Evaluation of cytotoxicity of the nanocarriers in C166 and A549 cells is shown in (D) and (E) after 24 h of incubation.

Figure 4A:
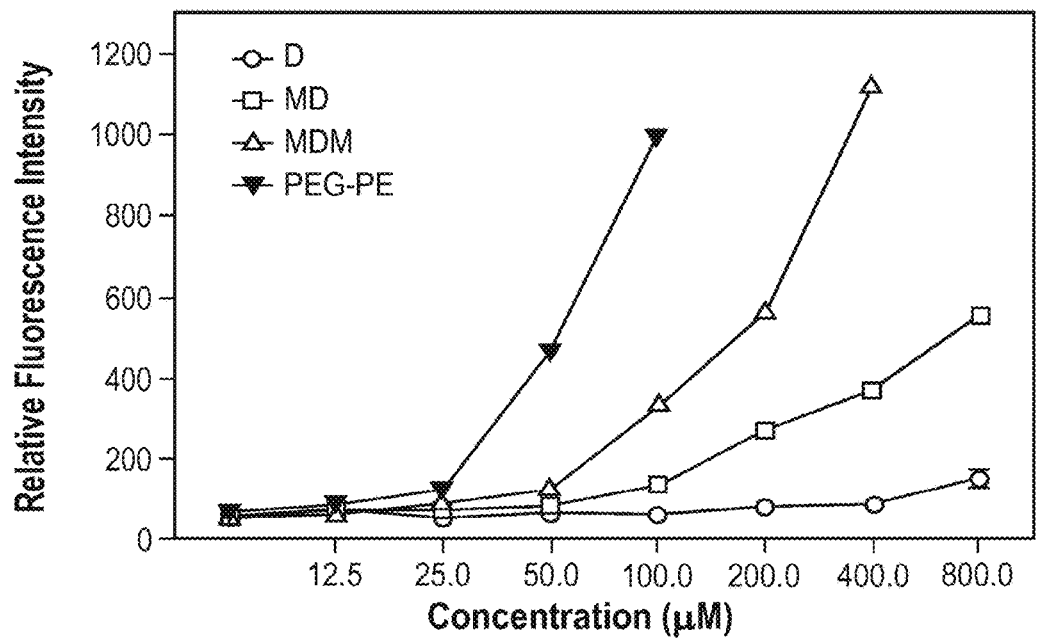
Figure 4B:
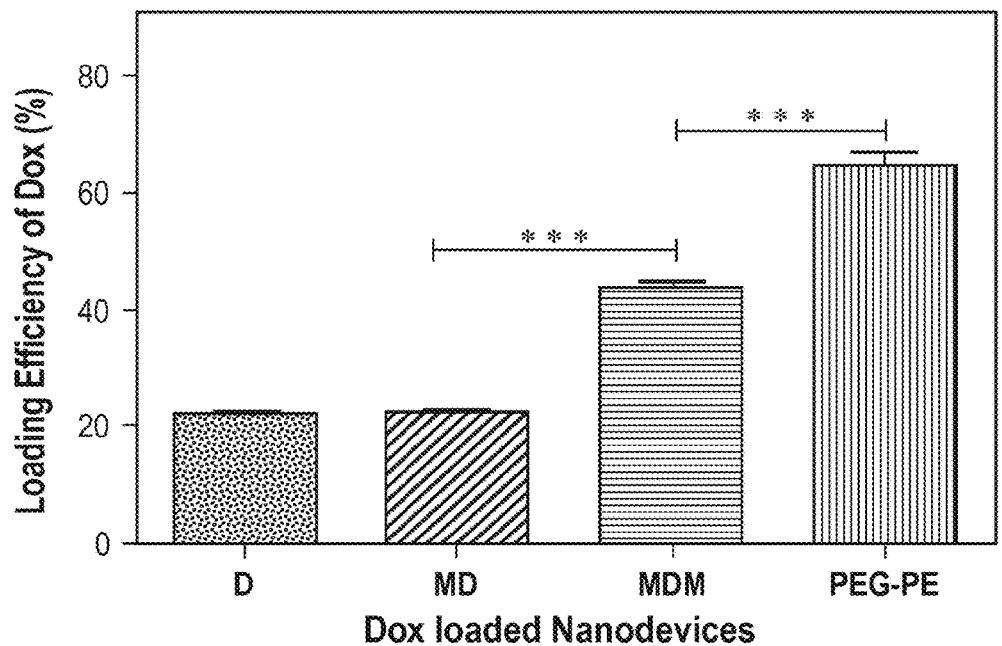
Figure 5A:
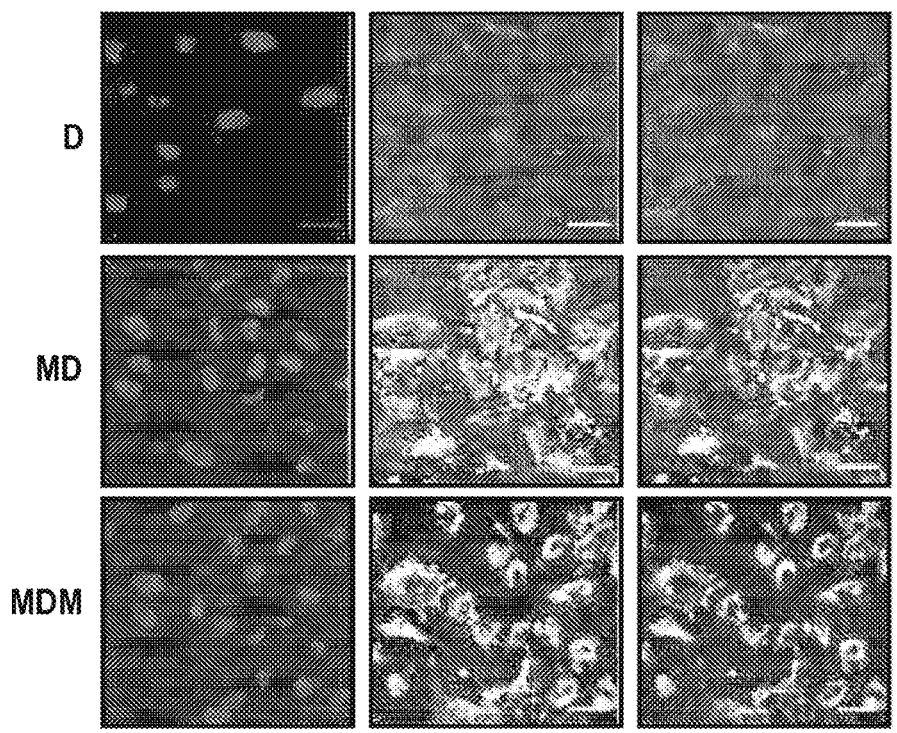
Figure 5B:
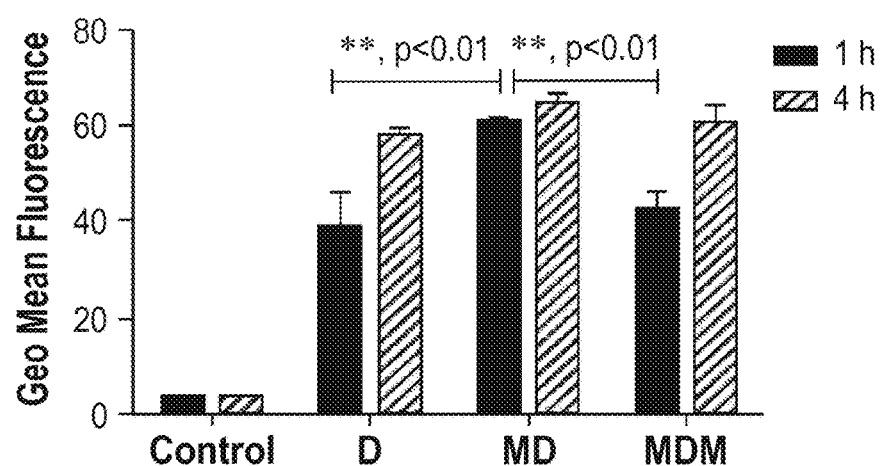
Figure 5C:
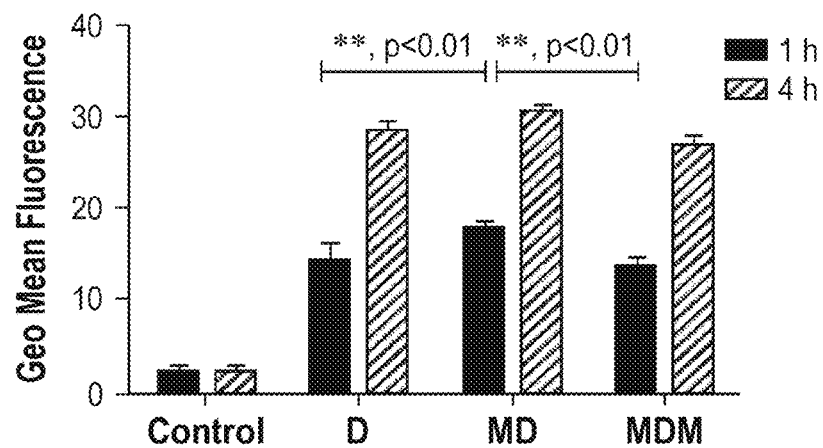
Figure 5D:
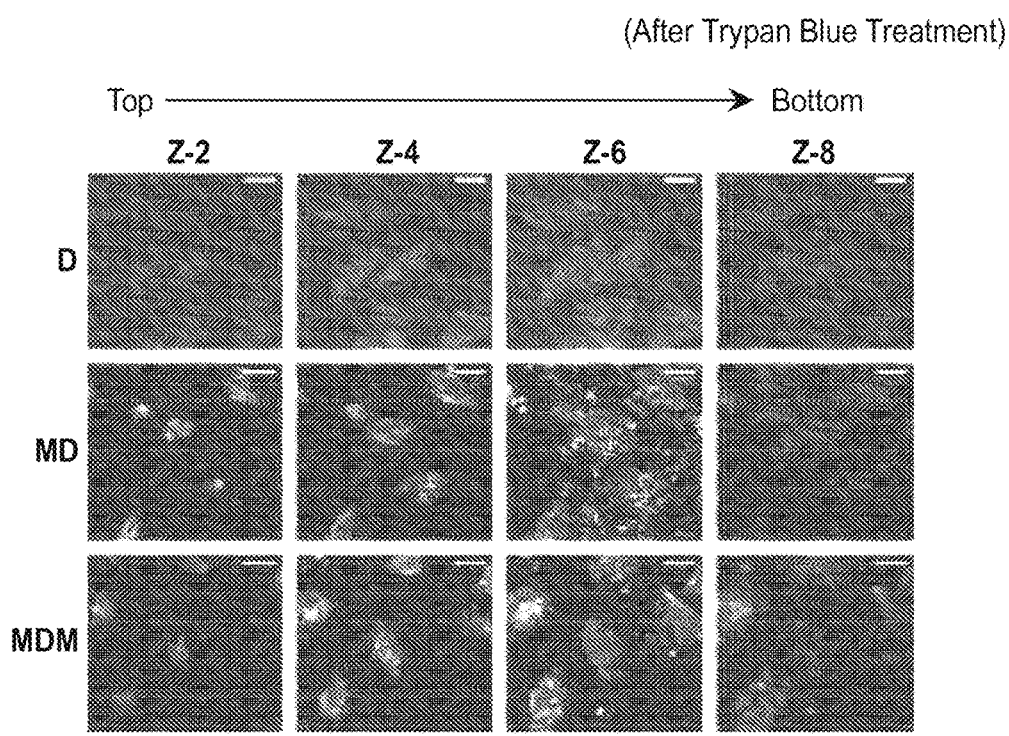
Figure 6A:
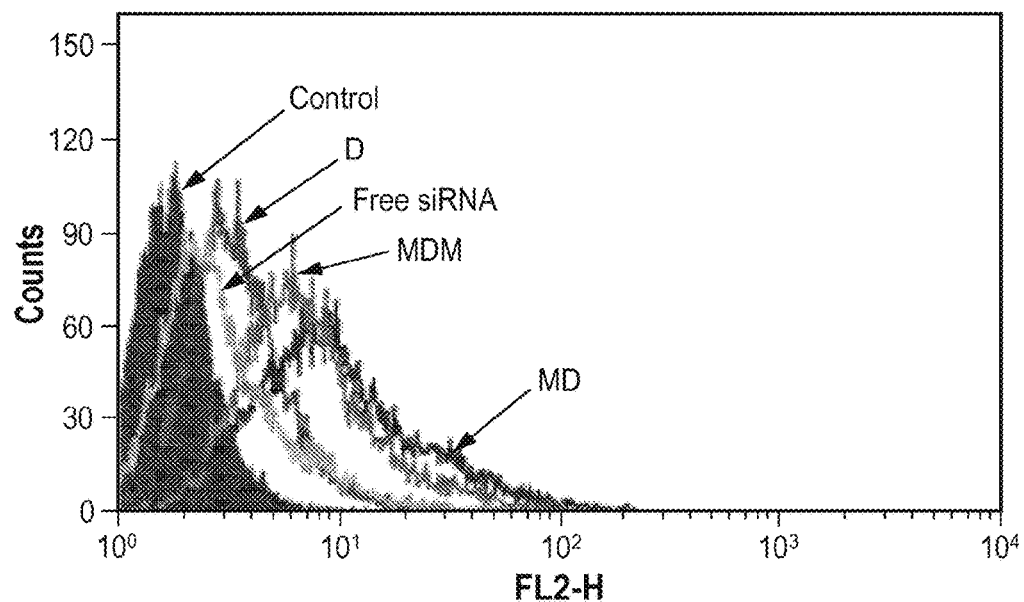
Figure 6B:
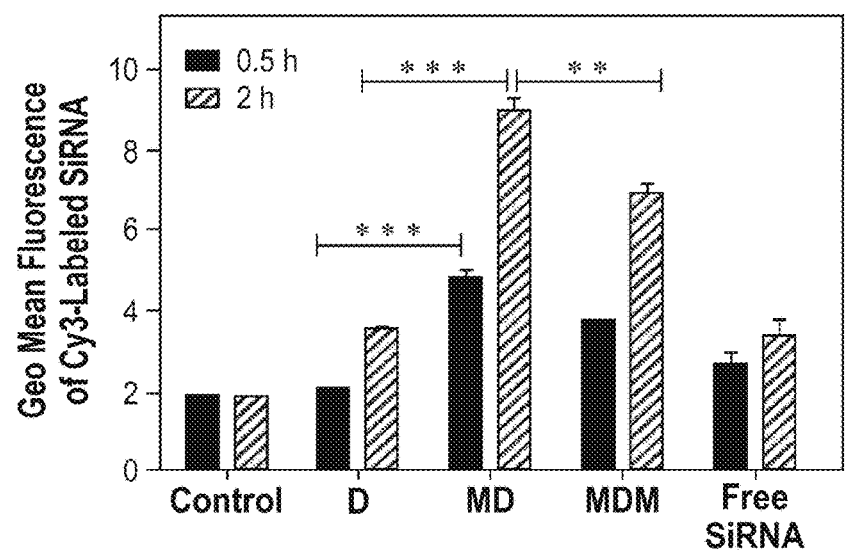
Figure 6C:
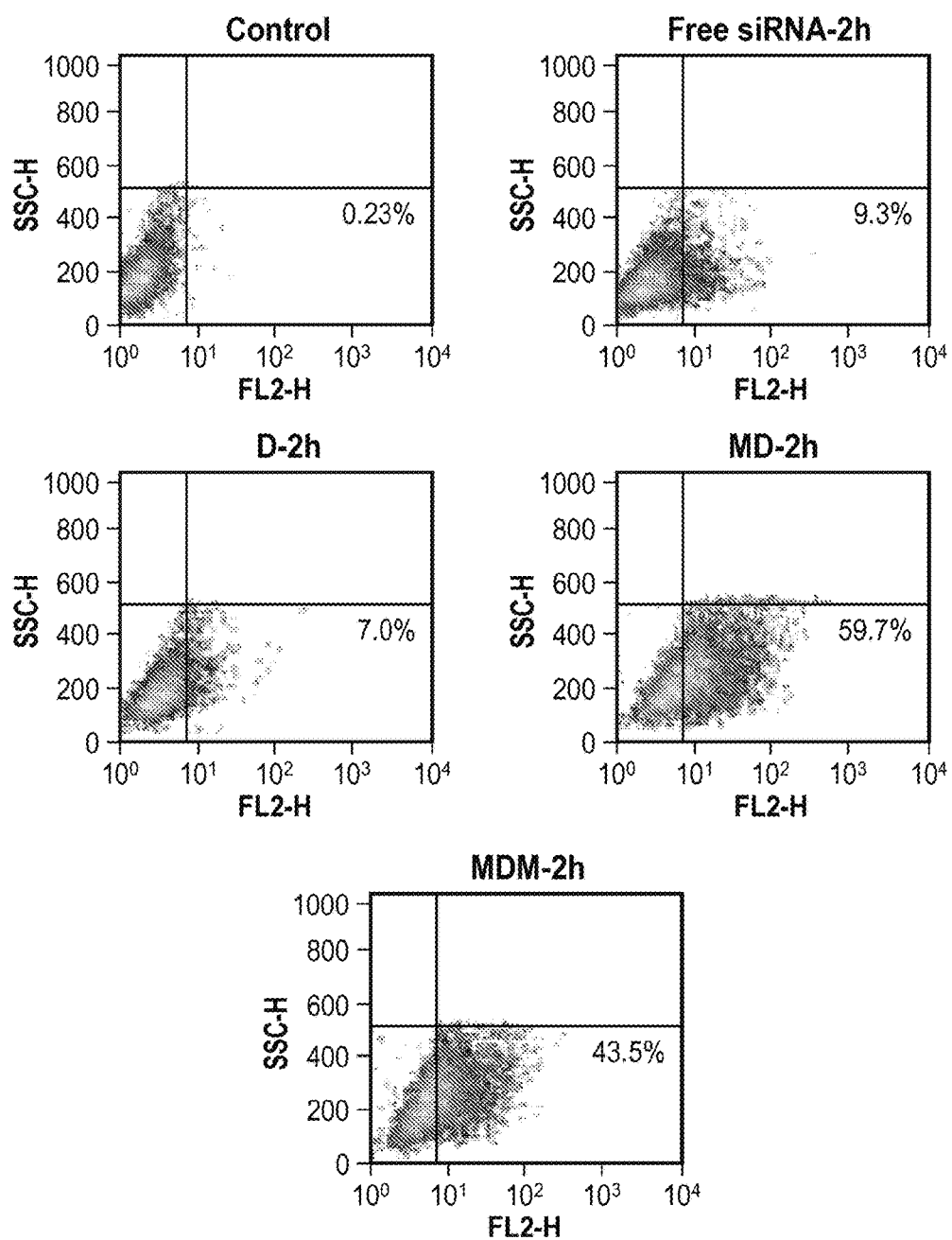
Figure 6D:
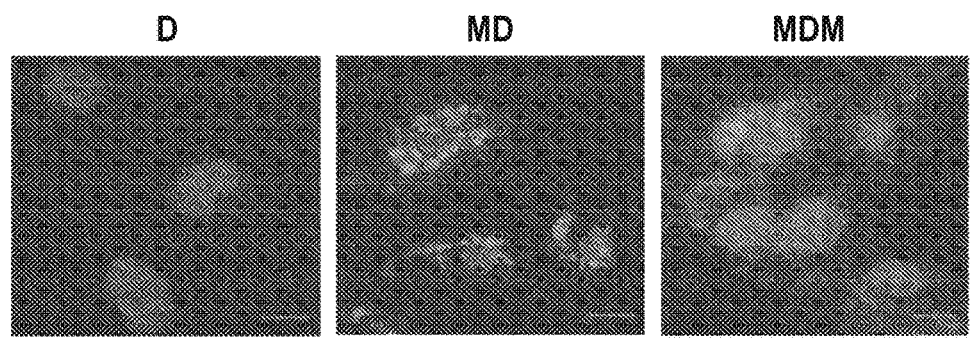

FIG. 4 illustrates an evaluation of loading efficiencies of co-polymers and mixed micellar systems. (A) Shown are determinations of critical micelles concentrations by the pyrene incorporation method, and (B) determinations of doxorubicin-loading efficiencies of the nanocarriers.

FIG. 5 illustrates the cellular uptake of nanocarriers (FITC-labeled) in A549 cells. Cells were incubated with MDM or MD for 2 h for visualization by confocal microscopy (A) and for 1 h and 4 h time periods for analysis by flow cytometry (B and C). Trypan blue was added for the purpose of quenching the surface associated fluorescence (C). (D) Selected images are shown of the cells in the XY plain at consecutive Z-axis (Z-2,4,6,8).

FIG. 6 illustrates an evaluation of siRNA delivery efficiencies of the co-polymer compositions and the mixed micellar compositions. (A) Shown is a representative histogram plot, obtained from fluorescence-activated cell sorting analysis, showing the uptake of Cy5 labeled siRNA, condensed with polymers and micellar system at NM=10 after 2 h of incubation with A549 cells. (B) Shown is the cellular uptake/delivery of Cy3-labeled siRNA-co-polymer dendriplexes, measured by the geometric mean of fluorescence, obtained from FACS analysis at 0.5 h and 2 h time points. (C) Representative dot plots are shown, as obtained from FACS analysis, showing the cells labeled with Cy5-siRNA, delivered by various siRNA•co-polymer dendriplexes. (D) Shown are the confocat laser scanning microscope (CLSM) images of siRNA-dendriplexes•dosed-A549 cells, after incubation for 2 h. Cell nuclei were stained with Hoechst 33342. Both FACS and microscopy studies were performed at siRNA concentrations of 100 nM (1:1 mixture of Cy5-labeled siRNA and scramble siRNA) at N/P ratio of 10.

Figure 7A:
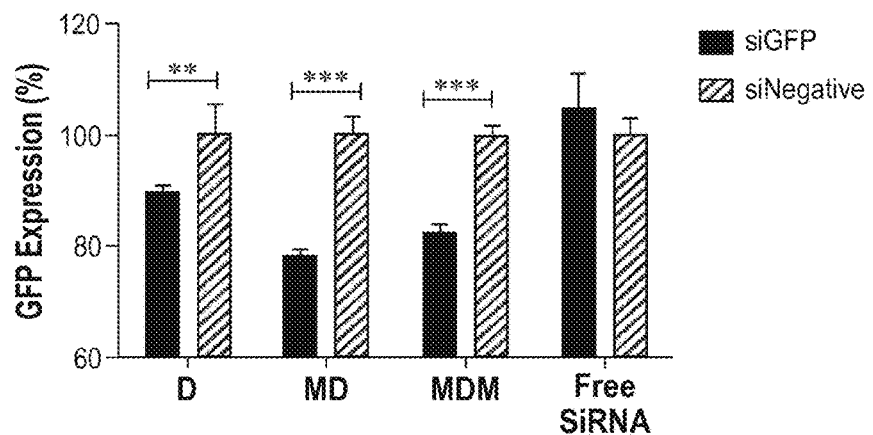

FIG. 7 illustrates the efficiency of down-regulating the target protein by siRNA-co-polymer dendriplexes. Green fluorescence protein-silencing siRNA (siGFP) (200 nM) was delivered to the C166-GFP cells (stably expressing GFP) via dendriplexes in co-polymer systems (at NIP ratio=10). (A) Geometric mean of fluorescence of the siGFP-treated cells (obtained from the histogram statistics in FAGS analysis) was plotted compared to the siNegative treated cells. (B) Shown is a fluorescence micrograph, demonstrating the GFP-protein down regulation effect of siGFP treatment. The nuclei were stained with Hoechst 33342.

FIG. 8 illustrates the Dox-delivery efficiency of the nanocarriers analyzed by flow cytometry. (A) Representative histogram plot, demonstrating the differences in the dox-labeling of the A549 cells treated with a fixed dose of dox (4 pg/mL) for 1 h, loaded in the nanocarriers. (B) Quantitative comparison of dox-loaded nanocarrier-mediated dox-delivery. Mean fluorescence of the treated cells (obtained by analyzing the histogram statistics) was plotted compared to control.

FIG. 9 illustrates an assessment of the co-delivery efficiency of nanocarriers by flow cytometry. (A) Shown is a quantitative comparison of the geometric mean of fluorescence from Dox and FAM-labeled siRNA, delivered to the A549 cells via Dox-loaded dendriplex systems. (B) A representative dot plot is shown, as obtained by FACS analysis, showing the difference in Dox- and FAM-siRNA-labeling in the cell populations.

Figure 10:
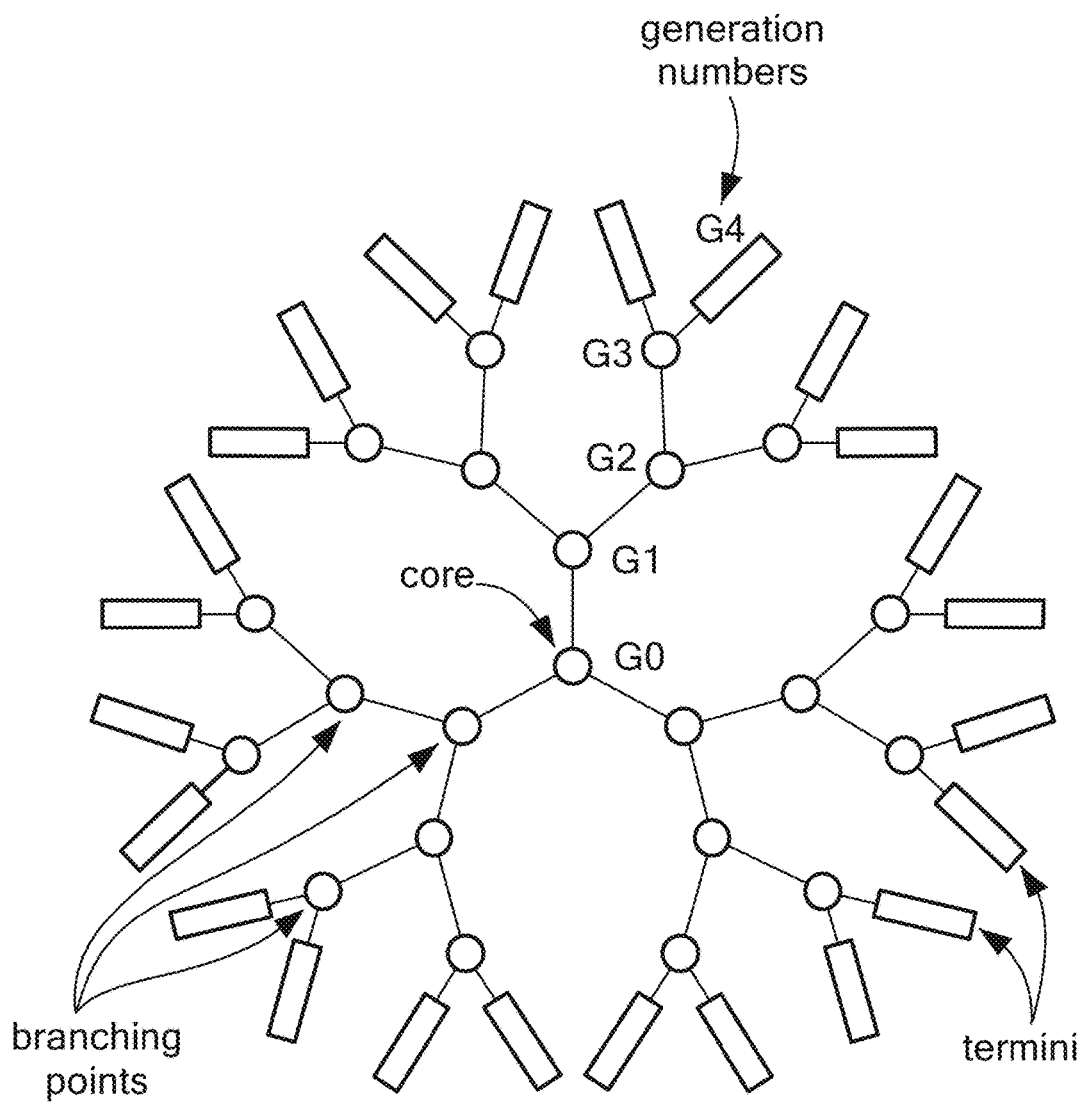

FIG. 10 is a schematic illustration of a dendrimer.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined and designed in a wide variety of different configurations, all of which are explicitly contemplated and made part of this disclosure.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to, plus or minus 10% of the particular term.

The use of the terms "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl or alkenyl or polyamino group, as defined below in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Unless expressly indicated otherwise, alkyl groups may be substituted, or unsubstituted, and if no designation is used, it is assumed that the alkyl group may be either substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein, the term haloalkyl is an alkyl group having one or more halo groups. In some embodiments, haloalkyl refers to a per-haloalkyl group. In some embodiments, alkyl refers to the alkyl side chain derived from lauric (C12), myristic (C14), palmitic (C16) or stearic (C18) acid.

Alkenyl groups are straight chain, branched or cyclic alkyl groups having 2 to about 20 carbon atoms, and further including at least one double bond. In some embodiments alkenyl groups have from 1-12 carbons or, typically, from 1-8 carbon atoms. Unless expressly indicated otherwise, alkenyl groups may be substituted or unsubstituted, and if no designation is used, it is assumed that the alkenyl group may be either substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=$CH_2$, C=$CH_2$, or C=$CHCH_3$. In some embodiments, the alkenyl group corresponds to the monounsaturated or polyunsaturated sidechain from palmitoleic (16:1 n-7), cis-vaccenic acid (18:1 n-7), oleic acid (18:1 n-9), linoleic acid (18:1 n-6), linoelaidic acid (18:1 n-3), arachidonic acid (20:4 n-6), eicosapentaenoic acid (20:5 n-3) or docosahexaenoic acid (22:6 n-3).

The terms "alkylene" and "alkenylene," alone or as part of another substituent means a divalent radical derived from an alkyl or alkenyl group, respectively, as exemplified by —$CH_2CH_2CH_2CH_2$—. For alkylene and alkenylene linking groups, no orientation of the linking group is implied.

The term "amine" (or "amino"), as used herein, refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —$NH_2$, methylamino, dimethylamino, ethylamino, diethylamino, propylamino, isopropylamino, phenylamino, benzylamino, and the like.

The term "amine" (or "amino"), as used herein, refers to A modified dendrimer-micelle (MDM) was prepared by mixing the modified dendrimer PAMAM G(4)-D-$PEG_{2K}$-DOPE (MD), as described below, with PEG-5K-DOPE at molar ratio of 1:1. These modified dendrimer MD and mixed micelles MDM were compared with PAMAM G(4)-dendrimers (D) throughout these examples.

"Cancer" refers to a broad group of disease involving unregulated cell growth and division. Non-limiting examples of cancers include leukemias, lymphomas, carcinomas, and other malignant tumors, including solid tumors, of potentially unlimited growth that can expand locally by invasion and systemically by metastasis. Examples of cancers include any of those described herein, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Patient" and "subject" are used interchangeably to refer to a mammal in need of treatment e.g., for cancer. Generally, the patient is a human. In some embodiments, the patient is a human diagnosed with cancer. In certain embodiments a "patient" or "subject" may refer to a non-human mammal used in screening, characterizing, and evaluating drugs and therapies, such as, a non-human primate, a dog, cat, rabbit, pig, mouse or a rat.

"Solid tumor" refers to solid tumors including, but not limited to, metastatic or non-metastatic tumors in bone, brain, liver, lungs, lymph node, pancreas, prostate, skin and soft tissue (sarcoma).

"Therapeutically effective amount" of a drug refers to an amount of a drug that, when administered to a patient with cancer, will have the intended therapeutic effect, e.g., alleviation, amelioration, palliation or elimination of one or more manifestations of cancer in the patient. A therapeutic effect does not necessarily occur by administration of one dose, and may occur only after administration of a series of doses. Thus, a therapeutically effective amount may be administered in one or more administrations.

"Administering" or "administration of" a drug to a subject or patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Treating," "treatment of," or "therapy of" a condition or patient refers to taking steps to obtain beneficial or desired results, including clinical results. Beneficial or desired clinical results include, but are not limited to, alleviation or amelioration of one or more symptoms of cancer; diminishment of extent of disease; delay or slowing of disease progression; amelioration, palliation, or stabilization of the disease state; or other beneficial results. Treatment of cancer may, in some cases, result in partial response or stable disease.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl (i.e., $C_1$-$C_6$) sulfonate and aryl sulfonate.

The Copolymer

According to one aspect, a co-polymer of formula A-L-D, or a pharmaceutically acceptable salt thereof is provided wherein A is a linear, branched or dendritic polyamine; D is a lipid; and L is a linker comprising a water soluble polymer; wherein L is connected to A at a first end through a first covalent bond and connected to D at a second end through a second covalent bond.

In some embodiments, the polyamine A is any of the polyamines described herein.

In some embodiments, the linker L comprises —$(R_4O)_n$—; where $R_4$ is $C_2$-$C_8$ alkylene, optionally substituted; and n is from 1 to 50.

In some embodiments, the lipid D is selected from the group consisting of a naturally occurring fat, wax, sterol, fat-soluble vitamin (such as vitamins A, D, E, and K), monoglyceride, diglyceride, triglyceride and phospholipid.

In some embodiments, the co-polymer is of formula (I)

A-B-C-D    (I)

or a pharmaceutically acceptable salt thereof, wherein
A is a poly(amidoamine) dendrimer (PAMAM);
B is selected from the group consisting of a bond, —CO—, —COO—, —CONR$_5$—, —CH$_2$CH$_2$CO—, —CH$_2$CH$_2$COO—, —CH$_2$CH$_2$CONR$_5$—, —SO$_2$— and —SO$_2$NR$_5$—;
C is —(R$_4$O)$_n$—;
D is F, EF or E(F)$_2$;
E is selected from the group consisting of a bond, —COO—, —CONR$_5$—, —CH$_2$CH$_2$COO—, —CH$_2$CH$_2$CONR$_5$—, —SO$_2$NR$_5$—;

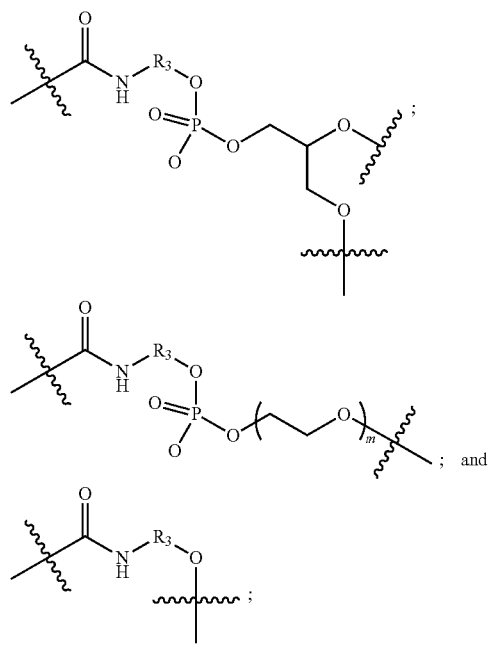

F is —CO—C$_6$-C$_{22}$-alkyl or —CO—C$_6$-C$_{22}$-alkenyl;
R$_3$ is C$_2$-C$_8$ alkylene, optionally substituted;
R$_4$ is C$_2$-C$_8$ alkylene, optionally substituted;
R$_5$ is hydrogen or C$_1$-C$_6$ alkyl, optionally substituted;
n is from 1 to 50; and
m is from 1 to 50.

The Polyamine "A" Moiety

The disclosed co-polymer includes a linear, branched or dendritic polyamine wherein the polyamine "A" is connected to a spacer "L" of the co-polymer "A-L-D" at a first end through a first covalent bond. In some embodiments of the co-polymer, A is G(4)-PAMAM. In some embodiments, A is G(4)-PAMAM, as will be described in greater detail below.

Without being bound by theory, the polyamine is believed to associate with siRNA due to its ability to form stable siRNA-polymer complex via electrostatic interaction under physiological condition. In some embodiments, once complexed, the disclosed co-polymer and polyamine portion of the complex therein protect siRNA from enzymatic degradation and can facilitate endocytosis and endosomal disruption. Some polyamines are toxic and or immunogeneic. However, incorporation into the co-polymers of the present technology, the toxicity and/or immunogenicity of some of the disclosed polyamines can be reduced.

In some embodiments, the polyamine that is utilized and incorporated into the co-polymer of the present technology is any known polyamine including those that have been reported for the delivery of siRNA. Non-limiting examples of such polyamines include protamine (Rossi, 2005, Nat Biotech 23:682-84; Song et al., 2005, Nat Biotech 23:709-17); polyethylenimines (PEIs), (Schiffelers et al., 2004, Nucl Acids Res 32:e149); polypropyleneimines (PPIs), (Taratula et al., 2009, J Control Release 140:284-93); poly-L-lysines (PLLs) (Inoue et al., 2008, J Control Release 126:59-66); polyarginines; chitosan; and dendrimers such as PAMAM dendrimers (Pan et al., 2007, Cancer Res. 67:8156-8163). The skilled artisan will realize that in general, any polycationic proteins or polyamino polymers may be of use as siRNA carriers.

In some embodiments, the polyamine is a dendrimer. Dendrimers have been described extensively (see, e.g., Tomalia, Advanced Materials 6:529 (1994); Angew, Chem. Int. Ed. Engl., 29:138 (1990). Dendrimers are synthesized as substantially spherical structures, having a core, branching points and termini (i.e., surface groups), where the dendrimer typically ranges from 1 to 20 nanometers in diameter. A nonlimiting illustration of a dendrimer is shown in FIG. 10.

The dendrimer core structures dictates several characteristics of the molecule such as the overall shape, density and surface functionality (see, e.g., Tomalia et al., Chem. Int. Ed. Engl., 29:5305 (1990)). Spherical dendrimers can have ammonia as a trivalent initiator core or ethylenediamine (EDA) as a tetravalent initiator core (see, e.g., FIG. 9). Recently described rod-shaped dendrimers (See, e.g., Yin et al., J. Am. Chem. Soc., 120:2678 (1998)) use polyethyleneimine linear cores of varying lengths; the longer the core, the longer the rod.

In some embodiments, the dendrimers disclosed or utilized herein include termini (i.e., surface groups) having a plurality of amino groups. In some embodiments, the dendrimers disclosed or utilized herein include termini having a plurality of amino, OH, —CO$_2$H, —Si—C$_1$-C$_6$-alkyl groups, succinic acid groups and combinations thereof. In some embodiments, the dendrimers disclosed or utilized herein include termini having a plurality of amino and OH groups. In some embodiments, the dendrimer A is covalently attached via a terminal —NH— or —O— group to the -L-D moiety of the co-polymer. In some embodiments, the dendrimer A is covalently attached via a terminal —NR$_5$—, —NH— or —O— group to the -B-C-D moiety of the co-polymer, where R$_5$ is hydrogen or C$_1$-C$_6$ alkyl, optionally substituted. In some embodiments, R$_5$ is hydrogen. In some embodiments, R$_5$ is methyl.

The dendrimers disclosed or utilized herein include one or more branch points, which are commonly designated as generations or "G." For example, in some embodiments, the dendrimer is G5 is a generation five poly (amidoamine) "PAMAM" dendrimer, although higher (e.g., G6, G7, G8, G9, G10 or higher), or lower (e.g., G4, G3, or G2) dendrimers may also be used. As described herein, the disclosed and utilized co-polymers are not limited to any particular dendrimer or PAMAM dendrimer. A nonlimiting illustration of a G2 PAMAM dendrimer is shown below having a 1,2-diaminoethyl core and branch points prepared from monomers having the structure: CH$_2$=CHCONHCH$_2$CH$_2$NH$_2$.

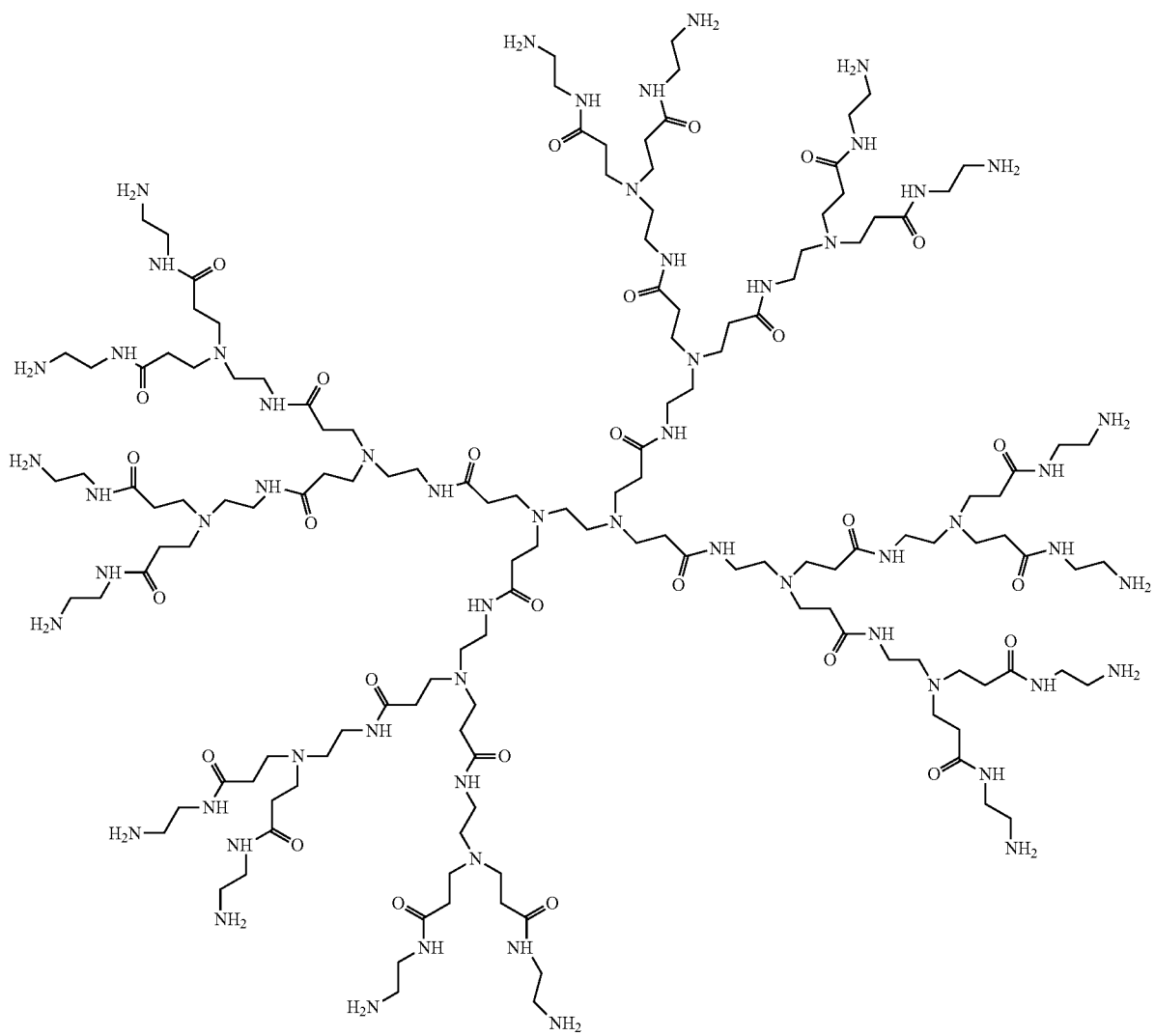 [SMILES: NCCNC(=O)CCN(CCNC(=O)CCN(CCNC(=O)CCN(CCC(=O)NCCN(CCC(=O)NCCN(CCC(=O)NCCN)CCC(=O)NCCN)CCC(=O)NCCN(CCC(=O)NCCN)CCC(=O)NCCN)CCN(CCC(=O)NCCN(CCC(=O)NCCN(CCC(=O)NCCN)CCC(=O)NCCN)CCC(=O)NCCN(CCC(=O)NCCN)CCC(=O)NCCN)CCC(=O)NCCN(CCC(=O)NCCN(CCC(=O)NCCN)CCC(=O)NCCN)CCC(=O)NCCN(CCC(=O)NCCN)CCC(=O)NCCN)CCC(=O)NCCN(CCC(=O)NCCN)CCC(=O)NCCN)CCC(=O)NCCN]

Cationic dendrimers have found applications as non-viral delivery vector for siRNA. The intracellular and intratumoral delivery of surface engineered poly(propyleneimine) dendrimers has been demonstrated where the siRNA-dendrimer nanocarriercomplexes were caged with dithiol containing cross-linker molecules, followed by coating with PEG. Liu, J. et al., *siRNA delivery systems based on neutral cross-linked dendrimers, Bloconjug Chem* 2012, 23, 174-83. The PEGylation and caging modification led to the extended systemic circulation of the RNA. Attachment of targeting peptide at the distal end of the PEG-chain directed nanocarrier the resulting complexes specifically to the cancer cells with improved gene-silencing ability. Hepatocyte-selective siRNA delivery has been achieved from lactosylated dendrimer (G-3)/a-cyclodextrin conjugates. In another study, PEG-modified PAMAM dendrimers were utilized for in vitro siRNA delivery and intramuscular gene silencing. Tang, Y.; et al., *Efficient in Vitro siRNA Delivery and intramuscular Gene Silencing Using PEG-Modified PAMAM Dendrimers.* Mol Pharm 2012, 9, 1812-21.

The "L" and "B-C" Moieties

As noted, the disclosed co-polymer includes a linear, branched or dendritic polyamine wherein the polyamine "A" is connected to a linker "L" of the co-polymer "A-L-D" at a first end through a first covalent bond. The linker L is connected to D, a hydrophobic moiety, at a second end through a second covalent bond.

In some embodiments the linker L includes the moiety —$(CH_2CH_2O)_n$—; where n is from 1 to 50. In some embodiments, the linker L of the co-polymer A-L-D is defined as "B-C" of co-polymer A-B-C-D, where B is selected from the group consisting of a bond, —CO—, —COO—, —$CONR_5$—, —$CH_2CH_2CO$—, —$CH_2CH_2COO$—, —$CH_2CH_2CONR_5$—, —$SO_2$— and —$SO_2NR_5$—; C is —$(R_4O)_n$—; $R_4$ is $C_2$-$C_8$ alkylene, optionally substituted; and n is from 1 to 50.

In some embodiments of the co-polymer A-B-C-D, B is —CO—. In some embodiments, B is —COO—. In some embodiments, B is —$CONR_5$—. In some embodiments, B is —$CH_2CH_2CO$—. In some embodiments, B is —$CH_2CH_2COO$—. In some embodiments, B is —$CH_2CH_2CONR_5$—. In some embodiments, B is —$SO_2$—. In some embodiments, B is —$SO_2NR_5$—.

In some embodiments of the co-polymer $R_5$ is hydrogen. In some embodiments of the co-polymer $R_5$ is methyl. In some embodiments of the co-polymer $R_5$ is ethyl. In some embodiments of the co-polymer $R_5$ is propyl. In some embodiments of the co-polymer $R_5$ is butyl.

In some embodiments of the co-polymer A-B-C-D, C is —$(R_4O)_n$— and $R_4$ is $C_2$ alkylene, optionally substituted. In some embodiments of the co-polymer A-B-C-D, $R_4$ is $C_3$ alkylene, optionally substituted. In some embodiments of the co-polymer A-B-C-D, $R_4$ is $C_4$ alkylene, optionally substituted. In some embodiments of the co-polymer A-B-C-D, $R_4$ is $C_{5-6}$ alkylene, optionally substituted. In some embodiments of the co-polymer A-B-C-D, $R_4$ is $C_{7-8}$ alkylene, optionally substituted. In some embodiments of the co-polymer, $R_4$ is —$CH_2CH_2$—. In some embodiments of the co-polymer, $R_4$ is —$CH_2CH_2CH_2$—. In some embodiments of the co-polymer, $R_4$ is —$CH_2CH_2CH_2CH_2$—. In some embodiments the $R_4$ is unsubstituted. In some embodiments the $R_4$ is substituted with $C_1$-$C_4$ alkyl. In some embodiments the $R_4$ is substituted with —$CO_2H$.

In some embodiments of the co-polymer A-B-C-D, C is —$(CH_2CH_2O)_n$— and n is from 1 to 50.

In some embodiments of the co-polymer A-B-C-D, n is from 1 to 5. In some embodiments of the co-polymer, n is from 6 to 10. In some embodiments of the co-polymer, n is from 11 to 20. In some embodiments of the co-polymer, n is from 21 to 30. In some embodiments of the co-polymer, n is from 31 to 40. In some embodiments of the co-polymer, n is from 41 to 50.

The "D," "E" and "F" Moieties

As noted, the disclosed co-polymer includes a linear, branched or dendritic polyamine wherein the polyamine "A" is connected to a linker "L" of the co-polymer "A-L-D" at a first end through a first covalent bond. The linker L is connected to D, a hydrophobic moiety, at a second end through a second covalent bond.

In some embodiments, the hydrophobic moiety D is —CO—$C_6$-$C_{22}$-alkyl or —CO—$C_6$-$C_{22}$-alkenyl. In some embodiments, the hydrophobic moiety D derives from a saturated fatty acid, monounsaturated fatty acid or polyunsaturated fatty acid. In some embodiments, the saturated fatty acid is lauric (C12), myristic (C14), palmitic (C16) or stearic (C18) acid. In some embodiments, the monounsaturated fatty acid is palmitoleic (16:1 n-7), cis-vaccenic acid (18:1 n-7) or oleic acid (18:1 n-9). In some embodiments, the monounsaturated fatty acid is oleic acid. In some embodiments, the polyunsaturated fatty acid is linoleic acid (18:1 n-6), linoelaidic acid (18:1 n-3), arachidonic acid (20:4 n-6), eicosapentaenoic acid (20:5 n-3) and docosahexaenoic acid (22:6 n-3). In some embodiments of the co-polymer, D comprises a dioleoylphosphatidyl ethanolamine (DOPE) moiety.

In some embodiments, D is F, EF or E(F)$_2$, where
E is selected from the group consisting of a bond, —COO—, —CONR$_5$—, —CH$_2$CH$_2$COO—, —CH$_2$CH$_2$CONR$_5$—, —SO$_2$NR$_5$—;

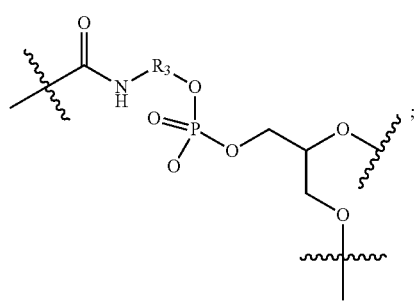

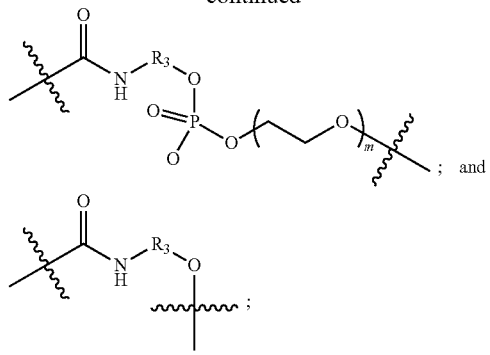

F is —CO—$C_6$-$C_{22}$-alkyl or —CO—$C_6$-$C_{22}$-alkenyl;
$R_3$ is $C_2$-$C_8$ alkylene, optionally substituted; and
m is from 1 to 50.

In some embodiments, E is

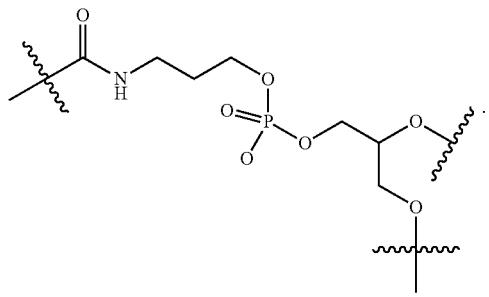 [SMILES: *OCC(COP(=O)(O)OCCCNC(*)=O)O*]

In some embodiments, E is

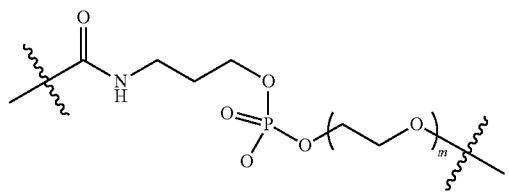

In some embodiments, E is

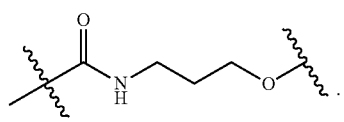 [SMILES: *OCCCNC(*)=O]

In some embodiments, E is

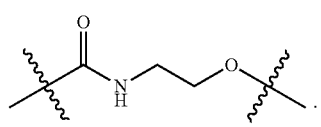 [SMILES: *OCCNC(*)=O]

In some embodiments of the co-polymer, D is E(F)$_2$ and E comprises sn-glycero-3-phosphoethanolamine.

In some embodiments of the co-polymer, $R_3$ is $C_2$ alkylene, optionally substituted. In some embodiments of the co-polymer, $R_3$ is $C_3$ alkylene, optionally substituted. In some embodiments of the co-polymer, $R_3$ is $C_4$ alkylene, optionally substituted. In some embodiments of the co-polymer, $R_3$ is —$CH_2CH_2$—. In some embodiments of the co-polymer, $R_3$ is —$CH_2CH_2CH_2$—. In some embodiments of the co-polymer, $R_3$ is —$CH_2CH_2CH_2CH_2$—.

In some embodiments of the co-polymer $R_5$ is hydrogen. In some embodiments of the co-polymer $R_5$ is methyl. In some embodiments of the co-polymer $R_5$ is ethyl. In some embodiments of the co-polymer $R_5$ is propyl. In some embodiments of the co-polymer $R_5$ is butyl.

In some embodiments, F is —CO—$C_6$-$C_{22}$-alkyl or —CO—$C_6$-$C_{22}$-alkenyl, where the $C_6$-$C_{22}$-alkyl or $C_6$-$C_{22}$-alkenyl derives from a saturated fatty acid, monounsaturated fatty acid or polyunsaturated fatty acid, as described herein, such as oleic acid.

In some embodiments, the spacer E is selected from the group consisting of a bond and groups consisting of phosphatidylserine or glycero-3-phosphoethanolamine. In some embodiments of the co-polymer, E comprises polyethylene glycol-dioleolphasphotidylethanolamine. In some embodiments, the spacer E comprises sn-glycero-3-phosphoethanolamine. Where the spacer E comprises sn-glycero-3-phosphoethanolamine, E will be covalently bound to two F groups, $C_6$-$C_{22}$-alkyl or $C_6$-$C_{22}$-alkenyl, where the F groups may be different or the same. In some embodiments of the co-polymer, F is oleoyl. In some embodiments F derives from a saturated fatty acid, monounsaturated fatty acid or polyunsaturated fatty acid, as described above.

In some embodiments, the co-polymer has the structure shown below where A is a PAMAM dendrimer, $R_1$ and $R_2$ are, independently, $C_6$-$C_{22}$-alkyl or $C_6$-$C_{22}$-alkenyl and n is 1 to 50.

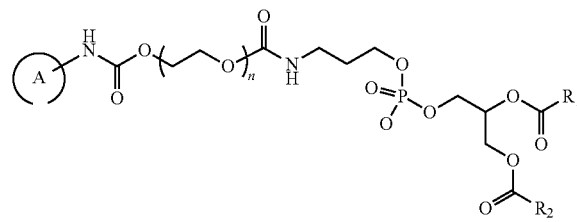

In some embodiments, $R_1$ and $R_2$ are $C_6$-$C_{22}$-saturated alkyl. In some embodiments, $R_1$ and $R_2$ are $C_6$-$C_{22}$-monounsaturated alkenyl. In some embodiments, $R_1$ and $R_2$ are $C_{18}$-monounsaturated alkenyl (i.e., derived from oleic acid). In some embodiments, $R_1$ and $R_2$ are $C_6$-$C_{22}$-polyunsaturated alkenyl.

In some embodiments, A is G2 PAMAM. In some embodiments, A is G3 PAMAM. In some embodiments, A is G4 PAMAM. In some embodiments, A is G5 PAMAM. In some embodiments, A is G6 PAMAM. In some embodiments, A is G7 PAMAM.

Micellar Compositions

In another aspect, a micellar composition is provided where the micellar composition includes any of the linear, branched or dendritic polyamine comprising co-polymers described herein. In some embodiments, the co-polymer is poly(ethylene glycol)-dioleoylphosphatidyl ethanolamine (PEG-DOPE) modified G(4)-PAMAM (i.e., G(4)-PAMAM-PEG-2K-DOPE).

In some embodiments, a "mixed" micellar composition is provided, comprising any one of the linear, branched or dendritic polyamine comprising co-polymers described herein, such as G(4)-PAMAM-PEG-2K-DOPE, and an "additional co-polymer" that generally lacks a linear, branched or dendritic polyamine moiety such as, for example, polyethylene glycol-phosphatidylethanolamine i.e., PEG-$_{5K}$-PE. Thus, in some embodiments, the additional co-polymer is PEG-$_{5K}$-PE.

In further embodiments, the "additional co-polymer" is any linear amphiphilic co-polymer, lipid or phospholipid. In some embodiments, the "additional co-polymer" is vitamin E. Other non-limiting exemplary "additional co-polymers" include PEG-phospholipid copolymers with variable lengths of the PEG block (i.e., component) of from about 750 to about 15,000 Da having any lipid component, such as a $C_8$-$C_{22}$ fatty acid, phospholipid, cardiolipin etc. In some embodiments, the additional co-polymer includes water-soluble non-toxic polymers (e.g., a polyvinylpyrrolidone, polyoxazoline, polyacrylamide, polyglycerol, polymorpholine component covalently bound to a lipid or phospholipid.

In some embodiments, the co-polymer and the additional co-polymer are in a ratio of from about 1:0.1 to about 1:10. In some embodiments, the co-polymer and the additional co-polymer are in a ratio of about 1:0.5. In some embodiments, the co-polymer and the additional co-polymer are in a ratio of about 1:0.75. In some embodiments, the co-polymer and the additional co-polymer are in a ratio of about 1:1. In some embodiments, the co-polymer and the additional co-polymer are in a ratio of about 1:2. In some embodiments, the co-polymer and the additional co-polymer are in a ratio of about 1:5. In some embodiments, the co-polymer and the additional co-polymer are in a ratio of about 1:10.

Interfering RNA

In some embodiments, the micellar composition or the "mixed" micellar composition further comprises siRNA i.e., one or more siRNA species.

The siRNA species to be delivered will be readily determined by the skilled artisan according to the disease state to be treated. Many siRNA species against a wide variety of targets are known in the art, and any such known siRNA may be combined with the disclosed compositions and delivered according to the methods disclosed herein.

Tens of thousands of siRNA sequences directed to mRNAs associated with a broad variety of disease states are known in the art and may be obtained from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mints Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNA Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be combined with the claimed compositions and delivered according to the claimed methods.

In one embodiment, the siRNA molecule binds to an mRNA that encodes at least part of a peptide or protein whose activity promotes tumorigenesis, angiogenesis, cell proliferation, or anti-apoptosis in the breast tissue of a subject, e.g., a mammal, human, etc. Such may be the case when the mRNA molecule encodes a protein in a pro-tumorigenic pathway, pro-angiogenesis pathway, pro-cell proliferation pathway, or anti-apoptotic pathway. For example, the protein can be an EGFR pathway protein, Raf-1 pathway protein, mTOR pathway protein, VEGF pathway protein, HIF-1 alpha pathway protein, Her-2 pathway protein, MMP pathway protein, PDGF pathway protein, or Cox-2 pathway protein. In one embodiment, the protein is one of the following: EGFR, Raf-1, mTOR, VEGF, HIF-1 alpha, Her-2, MMP-9, PDGF, or Cox-2.

By way of example, but not by way of limitation, in one embodiment, the composition described herein comprises one or more of an siRNA molecule (sense: 5'-CUGUAGA-CACACCCACCCACAUACA-3', antisense: 5'-UGUAU-GUGGGUGGGUGUGUCUACAG-3') that binds to an mRNA molecule that encodes human VEGF protein, an siRNA molecule (sense: 5'-CCAUCGAUGUCUA-CAUGAUCAUGGU-3', antisense: 5'-ACCAUGAUCAU-GUAGACAUCGAUGG-3') that binds to an mRNA molecule that encodes human EGFR protein, and/or an siRNA molecule (sense: 5'-GGUCUGGUGCCUGGU-CUGAUGAUGU-3', antisense: 5'-ACAUCAUCAGACCA-GGCACCAGACC-3'-3') that binds to an mRNA molecule that encodes human Cox-2 protein. See e.g., the published U.S. Patent Application US2012/0071540 to P. Lu et al., entitled "Compositions and Methods Using siRNA Molecules and siRNA Cocktails for the Treatment of Breast Cancer."

Small-Molecule Drugs

In some embodiments, the micellar composition or the "mixed" micellar composition further comprises a small-molecule drug. In some embodiments, the small-molecule drug includes, but is not limited to, a chemotherapeutic drug, although the present technology is not limited by the nature of the small-molecule or chemotherapeutic drug.

In some embodiments, the chemotherapeutic drug is selected from a group consisting of, but not limited to, platinum complex, verapamil, podophylltoxin, carboplatin, procarbazine, mechloroethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, bleomycin, etoposide, tamoxifen, paclitaxel, taxol, transplatinum, 5-fluorouracil, vincristin, vinblastin, bisphosphonate (e.g., CB3717), chemotherapeutic agents with high affinity for folic acid receptors, ALIMTA (Eli Lilly), and methotrexate.

Other useful chemotherapeutic drugs are selected from the group consisting of nitrogen mustards, alkyl sulfonates, nitrosoureas, triazenes, folic acid analogs, COX-2 inhibitors, antimetabolites, pyrimidine analogs, purine analogs, platinum coordination complexes, tyrosine kinase inhibitors, proteosome inhibitors, camptothecins, hormones, vinca alkaloids, anthracyclines, gemcitabine, epipodophyllotoxins, taxanes, antimetabolites, alkylating agents, antibiotics, SN-38, antimitotics, anti-angiogenic and pro-apoptotic agents, particularly doxorubicin, methotrexate, taxol, CPT-11, camptothecans, proteosome inhibitors, mTOR inhibitors, HDAC inhibitors, tyrosine kinase inhibitors and the like. In some embodiments, the chemotherapeutic drug is doxorubicin.

The compositions of the present disclosure can be used with a therapeutically effective amount of other chemotherapeutic drugs. These include chemotherapeutic drugs that impede or block tumorigenesis, angiogenesis, cell proliferation, or by way of example, but not by way of limitation, anti-apoptosis in the breast tissue of a subject, e.g., mammal. In one embodiment, the chemotherapeutic drug impedes or blocks the activity of a peptide or protein whose activity promotes tumorigenesis, angiogenesis, cell proliferation, or anti-apoptosis in the breast tissue of the mammal. For example, it may impede or block the activity of a peptide or protein that causes or promotes the growth of a breast cancer or causes or promotes its metastasis. In one embodiment, it impedes or blocks the activity of a protein that is a pro-tumorigenic pathway protein, a pro-angiogenesis pathway protein, a pro-cell proliferation pathway protein, or an anti-apoptotic pathway protein. Such proteins include, but are not limited to, an EGFR pathway protein, Raf-1 pathway protein, mTOR pathway protein, VEGF pathway protein, HIF-1 alpha pathway protein, Her-2 pathway protein, MMP pathway protein, PDGF pathway protein, or Cox-2 pathway protein. Particular examples of proteins that may be targeted by the therapeutic agent are: EGFR, Raf-1, mTOR, VEGF, HIF-1 alpha, MMP-9, PDGF, or Cox-2.

Suitable chemotherapeutic drugs are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Synthesis

The present section provides a general description of the synthesis, formation and use of the co-polymers and micellar compositions as described herein. In some embodiments, the preparation of PAMAM dendrimers is performed according to a typical divergent (building up the macromolecule from an initiator core) synthesis. It can involve e.g., a two-step growth sequence that includes of a Michael addition of amino groups to the double bond of methyl acrylate (MA) followed by the amidation of the resulting terminal carbomethoxy group with ethylenediamine (EDA).

In the first step of this process, a core compound such as EDA or ammonia is allowed to react under an inert nitrogen atmosphere with MA at 47 degrees C. for 48 hours. The resulting compound is referred to as generation=0, the star-branched PAMAM tri-ester. The next step involves reacting the tri-ester with an excess of EDA to produce the star-branched PAMAM tri-amine (G=O). This reaction is performed under an inert atmosphere (nitrogen) in methanol and may require 48 hours at 0 degree C. Reiteration of this Michael addition and amidation sequence produces generation=1.

Preparation of this tri-amine completes the first full cycle of the divergent synthesis of PAMAM dendrimers. Repetition of this reaction sequence results in the synthesis of larger generation (G=1-5) dendrimers (i.e., ester- and amine-terminated molecules, respectively). For example, the second iteration of this sequence produces generation 1, with an hexa-ester and hexa-amine surface, respectively. The same reactions are performed in the same way as for all subsequent generations from 1 to 9, building up layers of branch cells.

Various dendrimers can be synthesized based on the core structure, e.g., EDA or ammonia, that initiates the polymerization process. These core structures dictate several important characteristics of the dendrimer molecule such as the overall shape, density, and surface functionality (see, e.g., Tomalia et al., Angew. Chem. Int. Ed. Engl., 29:5305 (1990)). Spherical dendrimers derived from ammonia possess trivalent initiator cores, whereas EDA is a tetra-valent initiator core. Recently, rod-shaped dendrimers have been reported which are based upon linear poly(ethyleneimine) cores of varying lengths the longer the core, the longer the rod (see, e.g., Yin et al., J. Am. Chem. Soc., 120:2678 (1998)). All such core structures are encompassed by the co-polymers described herein.

In some embodiments, dendrimers comprise a protected core diamine. In some embodiments, the protected initiator core diamine is $NH_2$—$(CH_2)_n$—NHPG, (n=1-10). In other embodiments, the initiator core is selected from the group comprising, but not limited to, $NH_2$—$(CH_2)_n$—$NH_2$ (n=1-10), $NH_2$—$((CH_2)_nNH_2)_3$ (n=1-10), or unsubstituted or substituted 1,2-; 1,3-; or 1,4-phenylenedi-n-alkylamine, with a monoprotected diamine (e.g., $NH_2$—$(CH_2)_n$—NHPG) used during the amide formation of each generation. In these approaches, the protected diamine allows for the large scale production of dendrimers without the production of non-uniform nanostructures that can make characterization and analysis difficult. By limiting the reactivity of the diamine to only one terminus, the opportunities of dimmer/polymer formation and intramolecular reactions are obviated without the need of employing large excesses of diamine. The terminus monoprotected intermediates can be readily purified since the protecting groups provide suitable handle for productive purifications by classical techniques like crystallization and or chromatography.

The protected intermediates can be deprotected in a deprotection step, and the resulting generation of the dendrimer subjected to the next iterative chemical reaction without the need for purification. The present technology is not limited to a particular protecting group (PG). Indeed a variety of protecting groups are contemplated including, but not limited to, t-butoxycarbamate (N-t-Boc), allyloxycarbamate (N-Alloc), benzylcarbamate (N-Cbz), 9-fluorenylmethylcarbamate (FMOC), or phthalimide (Phth). In some embodiments, the protecting group is benzylcarbamate (N-Cbz).

The dendrimers may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magnetic resonance spectroscopy, high performance liquid chromatography (HPLC) size exclusion chromatography (SEC) (equipped with multi-angle laser light scattering, dual UV and refractive index detectors), capillary electrophoresis and gel electrophoresis. These analytical methods assure the uniformity of the dendrimer population and are important in the quality control of dendrimer production for eventual use in in vivo applications.

Pharmaceutical Compositions

In another aspect, compositions e.g., "pharmaceutical compositions" are provided comprising and an effective amount of a co-polymer as described herein, siRNA, a small-molecule drug or both an siRNA and a small molecule drug. In some embodiments, the composition further includes at least one pharmaceutically acceptable excipient.

Pharmaceutical compositions comprising co-polymer as described herein, siRNA, and/or a small-molecule drug can be formulated for different routes of administration, including intravenous, intraarterial, pulmonary, rectal, nasal, vaginal, lingual, intramuscular, intraperitoneal, intracutaneous, transdermal, intracranial, subcutaneous and oral routes. Other dosage forms include tablets, capsules, pills, powders, aerosols, suppositories, parenterals, and oral liquids, including suspensions, solutions and emulsions. All dosage forms may be prepared using methods that are standard in the art (see e.g., Remington's Pharmaceutical Sciences, $16^{th}$ ed., A. Oslo editor, Easton Pa. 1980).

In some embodiments, the co-polymer as described herein, siRNA, and/or a small-molecule drug are formulated in conjunction with appropriate salts and buffers to render delivery of the compositions in a stable manner to allow for uptake by target cells. Buffers also are employed when the co-polymer as described herein, siRNA, and optionally an additional co-polymer and/or a small-molecule drug are introduced into a patient. In some embodiments, an aqueous composition is used, comprising an effective amount of the co-polymer, siRNA, and optionally an additional co-polymer and/or a small-molecule drug, which are dispersed in a pharmaceutically acceptable carrier or excipient an aqueous medium. As used herein, "pharmaceutically acceptable carrier" includes any and all solvents, dispersion media, coatings, antibacterial and antifungal agents, isotonic and absorption delaying agents and the like. Sterile phosphate-buffered saline is one example of a pharmaceutically suitable excipient. Other suitable carriers and excipients are well-known to those in the art, see, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The co-polymer as described herein, siRNA, and optionally an additional co-polymer and/or a small-molecule drug may be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Methods of Use

Also provided is an effective method of using the copolymers, micellar compositions and mixed micellar compositions described herein for delivering siRNA and/or small molecule drugs to the interior of target cells (e.g., cancer cells). Thus, in some embodiments, methods of therapy are provided that comprise or require delivery of siRNA and/or small molecule drugs into a cell. In some embodiments, the small molecule drug is a chemotherapeutic drug e.g., doxorubicin.

In some embodiments, the co-polymer, siRNA and chemotherapeutic drug will be formulated to have a ratio where the amount of chemotherapeutic drug will significantly exceed the amount of siRNA that is formulated. In some embodiments, the co-polymer, siRNA and chemotherapeutic drug will be formulated to have a ratio of about (100-10,000):(0.001-10.0):(100-10,000). In some embodiments, the co-polymer, siRNA and chemotherapeutic drug have a ratio of about (10-1,000):1:(10-1,000). In some embodiments, the co-polymer, siRNA and chemotherapeutic drug have a ratio of about 1,000:1:1,000.

For example, in one non-limiting embodiment, the co-polymer, siRNA and chemotherapeutic drug will be formulated in 1 ml of aqueous solution having up to about 50 mg of micelle-forming or mixed micelle forming components (e.g., co-polymers) and from about 1 ng to about 10 micrograms of siRNA, and from about 0.1 mg to about 100 mg of a drug.

Without being bound by theory, the negatively charged siRNA is expected to complex with the with positively charged dendrimer portion of the co-polymers. The generally hydrophobic drug is expected to solubilize with the hydrophobic lipid portion of the micelle or mixed micelle. The co-polymer, siRNA and chemotherapeutic drug can be mixed e.g., incubated in any order. For example, a complex between siRNA and the dendrimer-containing co-polymers can be first formed in aqueous medium before the drug is subsequently added to form micelles. Alternatively, the drug can first be mixed with the dendrimer-containing co-polymers before being combined with the siRNA. The drug and siRNA can be combined followed by addition of the dendrimer-containing co-polymers. Finally, the siRNA, drug and dendrimer-containing co-polymers can be mixed at about the same time.

In another aspect, a method for treating cancer in a subject is provided, where the method comprises administering to the subject an effective amount of a composition comprising any of the co-polymers described herein, siRNA, a chemotherapeutic drug or both.

In another aspect, a method for delivering siRNA, an antineoplastic drug, or both into one or more cells of a subject is provided, where the method comprises administering to the subject an effective amount of a composition comprising any of the co-polymers described herein, siRNA and a chemotherapeutic drug.

In another aspect, a method is provided for treating cancer in a subject comprising administering to the subject an effective amount of any of the micellar compositions described herein.

In another aspect, a method is provided for delivering siRNA and a chemotherapeutic drug into one or more cells of a subject comprising administering to the subject an effective amount of any of the micellar compositions described herein The co-polymers described herein can be formulated, with siRNA and optionally an additional co-polymer and/or a small molecule cancer drug, for intravenous administration via, for example, bolus injection or continuous infusion. In some embodiments, the targeted delivery complex is infused over a period of less than about 4 hours; in some embodiments, the infusion is over a period of less than about 3 hours. For example, the first 25-50 mg could be infused within 30 minutes, even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Additionally or alternatively, the active ingredient can be in powder form for constitution with a suitable vehicle, e.g., sterile pyrogen-free water, before use.

The co-polymers described herein, and siRNA, a small molecule cancer drug or both, may also be administered to a subject subcutaneously or by other parenteral routes. Moreover, the administration may be by continuous infusion or by single or multiple boluses. In some embodiments, co-polymers described herein, and siRNA, a small molecule cancer drug or both an siRNA and small molecule cancer drug is infused over a period of less than about 4 hours, or over a period of less than about 3 hours.

More generally, the dosage of an administered co-polymer described herein, and siRNA, a small molecule cancer drug or both an siRNA or small molecule cancer drug, for humans will vary depending upon such factors as the patient's age, weight, height, sex, general medical condition and previous medical history.

In some embodiments, methods and compositions are provided for the treatment of cancer. One of the major adverse effects associated with long-term chemotherapy is multi-drug resistance, mainly which is encoded by mdr-1 gene. A co-polymer comprising drug delivery system such as those described herein, that can simultaneously deliver chemotherapeutic drug and siRNA to the tumor, provides a promising approach for the treatment of cancer.

Cell proliferative disorders, or cancers, contemplated to be treatable with the methods include human sarcomas and carcinomas, including, but not limited to, fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the method is used to inhibit growth, progression, and/or metastasis of cancers, in particular those listed above.

The present technology thus generally described will be understood more readily by reference to the following examples which are provided by way of illustration and are not intended to be limiting of the present technology.

EXAMPLES

Materials

PAMAM Dendrimer, ethylenediamine core, generation 4, 10 weight % solution in methanol (G(4)-D) was purchased from SigmaAldrich. 1,2-dioleoyl-sn-glycero-3-phosphoethanolamine-N-[methoxy(polyethylene glycol)-5000](ammonium salt) (PEG-5K-DOPE), 1,2-dioleoyl-sn-glycero-3-phosphoethanolamine (DOPE) were purchased from Avanti Polar Lipids (AL, USA). NPC-PEG-2K-NPC was purchased from Laysan Bio (AL, USA). Geneticin (G-418), FAM-labeled negative control siRNA and silencer Cy-3-labeled GAPDH siRNA were purchased from Ambion Life Technologies Invitrogen (NY, USA). siRNA, targeting green fluorescence proteins (siGFP): 50 AUGAACUUCAGGGU-CAGCUdTdT-30 (sense), Non-targeting control siRNA (siNegative): 50-AGUACUGCUUACGAUACGGdTdT-30 (sense). Nuclease-free water was purchased from Qiagen (MD, USA). Doxorubicin HCl (DOX) was purchased from SigmaAldrich. The cellTiter-Blue Cell Viability Assay was purchased from Promega (WI, USA). Human alveolar adenocarcinoma cell line, A549, mouse yolk sac embryo cells, c-166, stably transfected with a plasmid reporter vector, pEGFP-N1, encoding for the enhanced GFP, were purchased from the American Type Culture Collection (ATCC). Dulbecco's modified Eagle's media (DMEM) and fetal bovine serum (FBS) was obtained from Gibco (Carlsbad, Calif.). Penicillinestreptomycin solution was obtained from CellGro (VA, USA). Mitotracker deep red FM and Hoechst 33342 were purchased from Molecular Probes Inc. (Eugene, Oreg.). Paraformaldehyde was from Electron Microscopy Sciences (Hatfield, Pa.). Fluoromount-G was from Southern Biotech (Birmingham, Ala.). The CellTiter 96 Aqueous One Solution Cell Proliferation Assay kit was purchased from Promega (Madison, Wis.). The Trypan blue solution was obtained from Hyclone (Logan, Utah).

Example 1. Synthesis, Purification and Characterization of the Disclosed Co-Polymers Described, illustrated and tested herein are "mixed" dendrimers or micelles thereof, (MDM), modified dendrimers PAMAM G(4)-D-PEG$_{2K}$-DOPE or micelles thereof, (MD), and PAMAM G(4)-dendrimers (D). MDM, MD and D are referred to herein, individually and collectively, as "nanocarriers." The term "dendriplex" refers to a complex formed from any of the nanocarriers described herein and siRNA, and optionally a small-molecule drug. The term "micelle" is used according to its generally accepted meaning.

The "mixed" modified dendrimer-micelles (MDM) were prepared by mixing modified dendrimers PAMAM G(4)-D-PEG$_{2K}$-DOPE (MD), an exemplary "co-polymer," or micelles thereof, with PEG-5K-DOPE, an exemplary "additional co-polymer," at a molar ratio of about 1:1. MDM and MD were compared against PAMAM G(4)-dendrimers (D) throughout these examples.

The triblock copolymer MD was synthesized as described herein. The starting polymer NPC-PEG2K-DOPE was synthesized following methods known in the art. Briefly, into the solution of NPC-PEG2K-NPC (1 g, 0.5 mmol) in chloroform, DOPE (37.2 mg, 0.05 mmol) solution in chloroform mixed with 20 mL of triethylamine was added drop wise. The reaction mixture was stirred overnight at room temperature. The following day, the reaction mixture was evaporated using rotary evaporator and freeze-dried to remove traces of solvent. The dry crude reaction mixture was dissolved in HCl solution (0.01M) and purified by gel filtration chromatography using C14B column. For the synthesis of G(4)-D-PEG2K-DOPE, a methanol solution of G(4)-D was evaporated in a pre-weighed vial and freeze-dried to remove traces of methanol. Into the solution of G(4)-D in DMF (42.9 mg, 3.02 mM), and triethylamine (10 mL) was added NPC-PEG-2K-DOPE (7.7 mg, 4.9 mM) in DMF. The reaction mixture was stirred overnight at room temperature. The DMF was removed by rotary evaporator. The resulting crude reaction mixture was dissolved in water and dialyzed against water using a cellulose ester membrane (MWCO. 12-14,000 kDa) and freeze-dried. G(4)-D-PEG-2K-DOPE was characterized by 1H nuclear magnetic resonance (NMR) spectroscopy using Varian 400 MHz spectroscope. The starting materials, G(4)-D and NPC-PEG2K-DOPE and the polymer was dissolved in d-methanol at 5e10 mg/mL for NMR spectroscopy analysis.

For the labeling of G(4)-D with FITC, into a solution of G(4)-D (42.9 mg, 3.0 mM) in DMF was added FITC-NHS (1.4 mg, 3.0 mM) in DMF. The reaction mixture was stirred at room temperature overnight and the solvent was removed by rotary evaporator, dialyzed (MWCO. 10 kDa) and freeze-dried. The FITC-G(4)-D was used to prepare FITC-MD following the above mentioned procedure. Solid products were dissolved in BHG buffer (5% glucose in 20 mM HEPES in RNAse-free water, pH 7.4) at concentration of 5 mg/mL for all experiments using siRNA.

Primary amine end groups of dendrimers were shown to react readily with activated acid groups (p-nitrophenylcarbonyl) functionalized PEG-DOPE copolymers. The reaction was high yielding, rapid and spontaneous. The dialysis of the reaction mixture using a cellulose ester membrane (MWCO 10 kDa) removed small molecule impurities. The G(4) D-anchored PEG-$_{2K}$-DOPE copolymer was characterized by $^1$H NMR spectroscopy. The characteristic peaks noted at different ppm values are as follows (where singlet, doublet, triplet, multiplets are noted as s, d, t, m respectively): For starting material NPC-PEG-$_{2K}$-DOPE, $^1$H NMR in CDCl$_3$. δ ppm 0.90 (t, 6H), 1.30-1.33 (d), 1.58-1.62 (m), 2.01-2.06 (m), 2.31-2.37 (m), 3.30-3.50 (m), 3.58-3.68 (m), 3.78-3.81 (m), 3.99-4.00 (m), 4.11-4.18 (m), 5.33-5.36 (m), 7.50 (d), 8.35 (d). The most shielded peak at δ ppm 0.90 (t, 6H) was from the two terminal CH$_3$ groups of the lipid chains. The sharp peak at 3.6 was from (CH$_2$CH$_2$)n group of PEG. The peak at δ ppm 5.33-5.36 (m) was characteristic of —CH═CH— proton signals. The two most deshielded doublets are from the 4-proton of p-nitrophenyl (NO$_2$—C$_6$H$_4$) group.

For G(4)-D, $^1$H NMR in CDCl$_3$. δ ppm 2.32-2.39 (m), 2.56-2.61 (m), 2.67-2.69 (t), 2.77-2.85 (m), 3.19-3.28 (m). For G(4)-D-PEG-$_{2K}$-DOPE, $^1$H NMR in CD$_3$OD. δ ppm 0.90 (t, 6H), 1.31-1.33 (d), 1.58-1.62 (m), 2.01-2.05 (m), 2.36-2.39 (m), 2.58-2.60 (m), 2.78-2.82 (m), 3.26-3.32 (m), 3.64 (s), 5.30-5.34 (m). The characteristic peaks of both the starting materials were present in G(4)-D-PEG-$_{2K}$-DOPE.

Example 2. Particle Size

Measurement of size and size distribution analysis of G(4)-D and MD were performed by dynamic light scattering (DLS) using a Coulter N4-Plus Submicron Particle Sizer (Coulter Corporation, Miami, Fla.). G(4)-D and MD were dissolved in water at 5 mg/mL for analysis of particle size. Size distribution was also confirmed by using a transmission electron microscopy (TEM) (Jeol, JEM-1010, Tokyo, Japan).

Particle size of MD, obtained by DLS was 56+/−2.5 nm was higher than the particle size of the parent G(4)-D (20+/−5.2 nm). The TEM pictures of the polymers, as shown in FIG. 2, demonstrated similar size range as analyzed by DLS.

Example 3. Preparation of Pegylated and DOX-Loaded Nanocarriers

The MDM solution was mixed gently and the volume was adjusted with BHG buffer to obtain the desired concentration. To prepare DOX-loaded nanocarriers D-Dox and MD-Dox, a pre-mixed solution of 1 mg of Dox (1.72 mMol) and 10 mL of triethylamine in methanol was added to the methanol solution of D, MD or a chloroform solution of PEG-PE (3.45 mM). For the preparation of MDM-Dox, 1 mg of Dox was mixed with a mixture of MD and PEG-PE at an equimolar ratio (1.73 mM). The organic solvent was evaporated and freeze-dried to remove the traces of solvent. The dry lipid film was hydrated in 500 mL of HBS to obtain a solution of Dox at a concentration of 2 mg/mL. The solutions were passed through a 0.2 mm syringe filter (Nalgene, N.Y.) and dialyzed in HBS in a cellulose ester membrane (MWCO. 12e 14,000 kDa) to remove unincorporated Dox.

Example 4. Preparation of Co-Polymer Dendriplexes, Gel Retardation and Ethidium Bromide Exclusion Assay G(4)-D and MD were diluted with BHG buffer to 10 mL at varying concentrations (at different N/P ratios) and incubated with 750 ng of siRNA (10 mL) for 20 min at room temperature for the formation of dendriplexes. For N/P calculations, the reported molecular weight and the surface charge of the G(4)-D were taken into consideration ruling out the possibility of incomplete branching. The dendriplexes were subjected to electrophoresis on a 0.8% agarose gel containing Ethidium Bromide (EtBr), using an E-Gel electrophoresis system (Invitrogen Life Technologies) and visualized under UV light. The complex-forming ability of polymers with siRNA was examined by a quenching method using EtBr. Free or siRNA complexed with polymers at different N/P ratios was incubated with 12 mg/mL of EtBr (ICN Biochemical, Aurora, Ohio) and the fluorescence intensity was measured at excitation/emission wavelengths of 540 and 580 nm respectively using 96-well plate reader (Synergy HT, Biotek). Fluorescence of EtBr in the absence of siRNA was considered background and was subtracted from the readings. The fluorescence of the siRNA-EtBr complex in the absence of polycations was considered as 100 and the % relative fluorescence was determined for different N/P ratios. Finally, the recovery of fluorescence after dissociation of complexes following the addition of heparin sulfate (10 units/mg of siRNA) was measured.

Example 5. Cell Culture

A549 cells and C166-GFP cells were grown in DMEM, supplemented with 10% fetal bovine serum and antibiotics (for C166-GFP cells, 0.2 mg/mL of geneticin and for A549 cells, 100 IU/mL of penicillin, streptomycin and 250 ng/mL amphotericin-B) at 37° C. with 5% $CO_2$.

Example 6. Flow Cytometry

After the initial passage in T-75 cm2 tissue culture flasks (Corning Inc., NY), for cellular uptake study of FITC-labeled nanocarriers, A549 cells were seeded in 6-well tissue culture plates. The following day, the cells were incubated with FITC-labeled G(4)-D, MD and MDM (w1.0 mM) in 2 mL of serum-free media for 1 h and 4 h incubation periods (the fluorescence was normalized before each experiment). The media were removed, the cells washed several times, trypsinized, suspended in 1 mL PBS and then centrifuged at 1000 rpm for 5 min. The cell pellet was suspended in PBS, pH 7.4 before analysis using a BD FACS Caliber flow cytometer. The cells were gated using forward (FSC-H)- versus side-scatter (SSC-H) to exclude debris and dead cells before analysis of 10,000 cell counts. For the analysis of the quenching of fluorescence by Trypan blue, 10 mL of 0.4% trypan blue solution was added to 400 mL of cell suspension and analyzed again by FACS. For determination of siRNA-delivery efficiency, Cy-3 labeled siRNA was mixed with siNegative at a 1:1 mol ratio and used for complexation with G(4)-D, MD and MDM at an N/P ratio of 10. After incubation of dendriplexes for 20 min, the complexes were added to wells seeded with A549 cells in serum-free media. After 2 h incubation, the above mentioned post-incubation steps were performed before FACS analysis. For assessment of Dox-delivery efficiency, the A549 cells were incubated with Dox-loaded nanocarriers at a Dox concentration of 4 mg/mL for 2 h before analysis of the cellular Dox fluorescence by FACS. For assessment of co-delivery efficiency, A549 cells were treated with Dox-loaded G(4)-D, MD and MDM at a Dox concentration of 4 mg/mL, complexed with 100 nM of FAM-siRNA in serum-free media. The incubation period was 2 h before analysis of cell-associated fluorescence by FACS in FL1 and FL2 channels. The interference of Dox signal in the green channel was compensated by running the samples with Dox-loaded nanocarriers without FAM-siRNA. For representative histograms, the statistics to obtain the geometric mean of fluorescence and quadrant statistics for each cell sample were performed using BD Cell Quest Pro Software for all FACS experiments. For quadrant statistics, the axis, FL1-H and FL-2H, represent the FAM-siRNA and Dox labeling, respectively.

Example 7. Fluorescence Imaging by Confocal Microscopy

The following method was used for experiments involving the visualization of cells under the confocal microscope. After the initial passage in tissue culture flasks, A549 cells (40,000 cells on cover-slips) were grown on circular cover glasses placed in 12-well tissue culture plates in complete media. On the following day, for cellular uptake study using FITC-labeled nanocarriers, the cells were incubated with FITC-labeled dendrimer solutions (w1 mM) for 1 h in serum-free media, after normalization of FITC-fluorescence in each sample before addition. After the incubation, the cells were washed with PBS, added Hoechst 33342 (Molecular Probes, Ugene, Oreg., USA) at 5 mg/mL for 5 min, fixed with 4% para formaldehyde for 10 min at room temperature and the cover-slips were mounted cell-side down on superfrost microscope slides with fluorescence-free glycerol-based mounting medium (Fluoromount-G; Southern Biotechnology Associates) and viewed with a Zeiss Confocal Laser Scanning Microscope (Zeiss LSM 700) equipped with FITC filter (ex. 450-505 nm, 515-545 nm) for in vitro imaging. The z-Stacked images (slice thickness. 0.75 mm) were obtained by capturing serial images of the xy planes by varying the focal length of the same to image consecutive z-axis. For siRNA delivery, cells on cover-slips were incubated with the polymer-Cy-3-labeled siRNA complexes for 2 h, following the incubation procedure used for siRNA delivery in the flow cytometry section. The LSM picture files were analyzed using Image J software.

Example 8. GFP-Silencing

C166-GFP cells were seeded in 12-well plates at a density of $5 \times 10^4$/well, 24 h prior to the transfection. The complete media was replaced by serum-free DMEM. Anti-GFP-siRNA (siGFP) complexed with G(4)-D, MD and MDM at N/P ratio of 10, were added to cells at final siRNA concentration of 200 nM. A non-targeting control duplex (siGFP), was used as a control and siRNA was used corresponding to each siGFP treatment at same concentration. After 4 h of incubation, the media was removed and the cells were incubated in fresh complete media for additional 48 h. The cells were washed, detached by trypsinization and GFP down-regulation was analyzed by flow cytometry. To assess the GFP-silencing by fluorescence microscopy, C166-GFP cells were grown on microscope cover-slips (22 mm circle), placed in 12-well tissue culture plates at cell density of 40,000 on cover glass. The following day, the plates were washed with serum-free media and incubated with dendriplex and micellar dendriplexes of siGFP (200 nM) at an N/P ratio of 10 for 4 h in 1 mL serum free media. After 4 h of incubation, the media was removed and the cells were incubated in fresh complete media for an additional 48 h. The next steps followed were as written in the section of fluorescence imaging by confocal microscopy and studied with a Nikon Eclipse E400 microscope with a UV filter (ex. 330-380 nm) for Hoechst staining and with the FITC filter (ex. 465-495) for the GFP signal.

Example 9. siRNA Binding

To assess the siRNA binding ability of the synthesized polymers, gel retardation and ethidium bromide exclusion assays were performed. In gel retardation assay, MD and MDM condensed siRNA as effectively as parent G(4)-D. Complete binding of siRNA with polymer began at a molar ratio of nitrogen in the carrier/phosphate in the siRNA (N/P) of 2/1. See FIG. 3A. The ethidium bromide exclusion assay demonstrated the complete condensation or quenching of the siRNA at an N/P ratio of 2/1. See FIG. 3B. The fluorescence intensity of the naked siRNA in the presence of ethidium bromide was considered as non-quenching and an emission of maximum fluorescence. The amount of naked siRNA in the system decreased resulting in a decreased fluorescence with the gradual increase in the concentration of the polymers (N/P=0-2). See FIG. 3B. Upon the addition of heparin, the fluorescence reached its maximum level. See FIG. 3C.

Example 10. Cytotoxicity

Cytotoxicity of the dendrimers and modified dendrimers were determined with a CellTiter 96 Aqueous One Solution Cell Proliferation Assay kit following the manufacturer's protocol. C166-GFP and A549 cells were seeded in 96-well tissue culture plates at $5 \times 10^3$/well. The next day, the cells were incubated with G(4)-D, MD and MDM at varying concentrations (0-1000 nM) for 24 h. At the end of the incubation period, the cells were washed with PBS and supplemented with 100 mL of the serum free DMEM followed by the addition of 20 mL of Cell Titer Blue Assay Reagent. The cells were incubated with the reagent for 2 h. The fluorescence intensity was measured with a multi-detection microplate reader (Biotek, Winooski, Vt.) using 530/590 ex/em wavelengths. Cells treated with medium only were considered 100% viable.

Figure 3A:
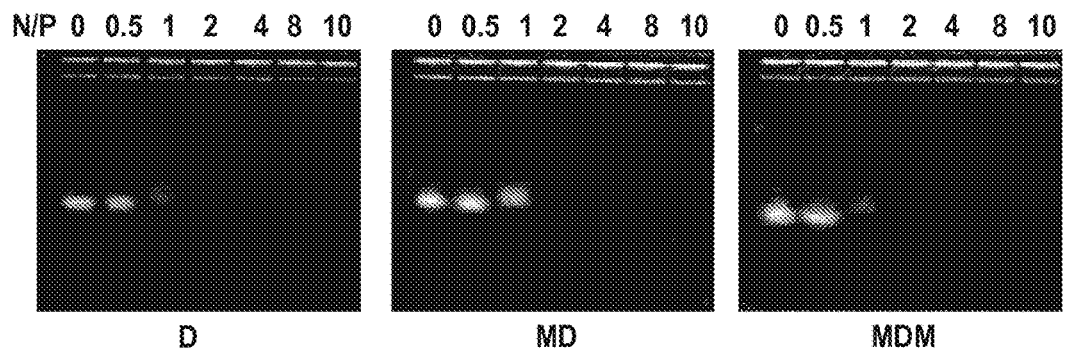
Figure 3B:
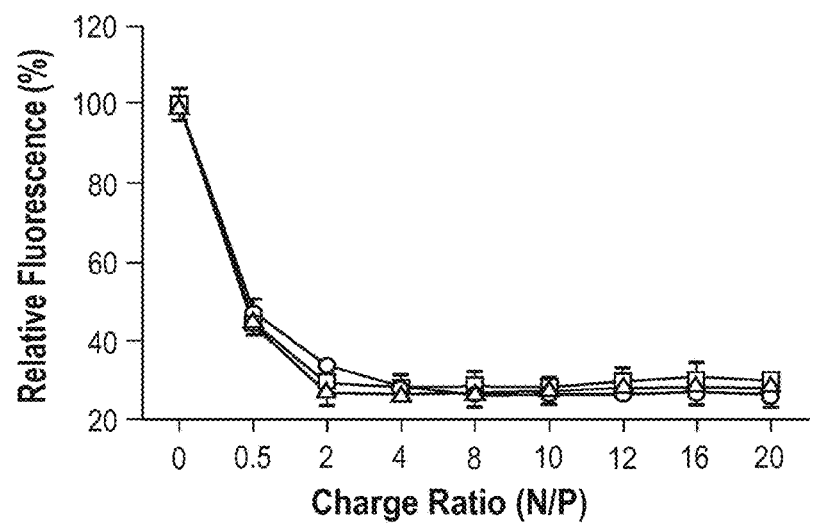
Figure 3C:
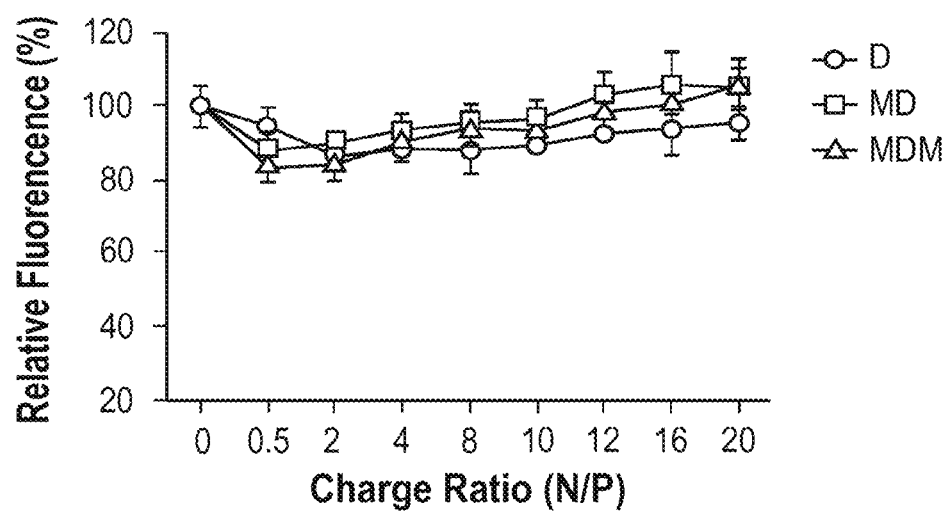
Figure 3D:
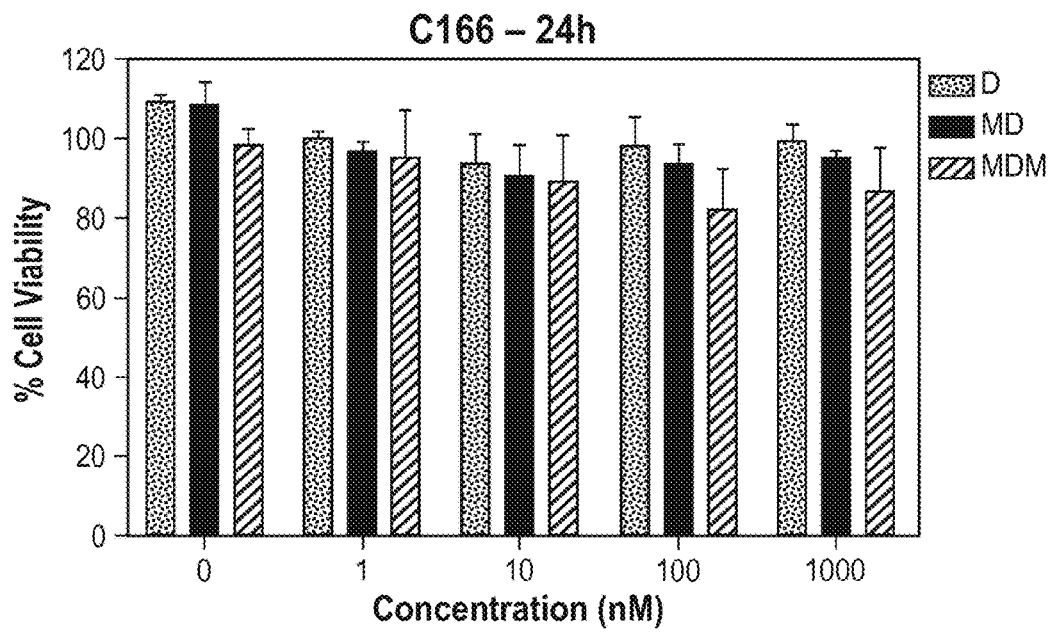
Figure 3E:
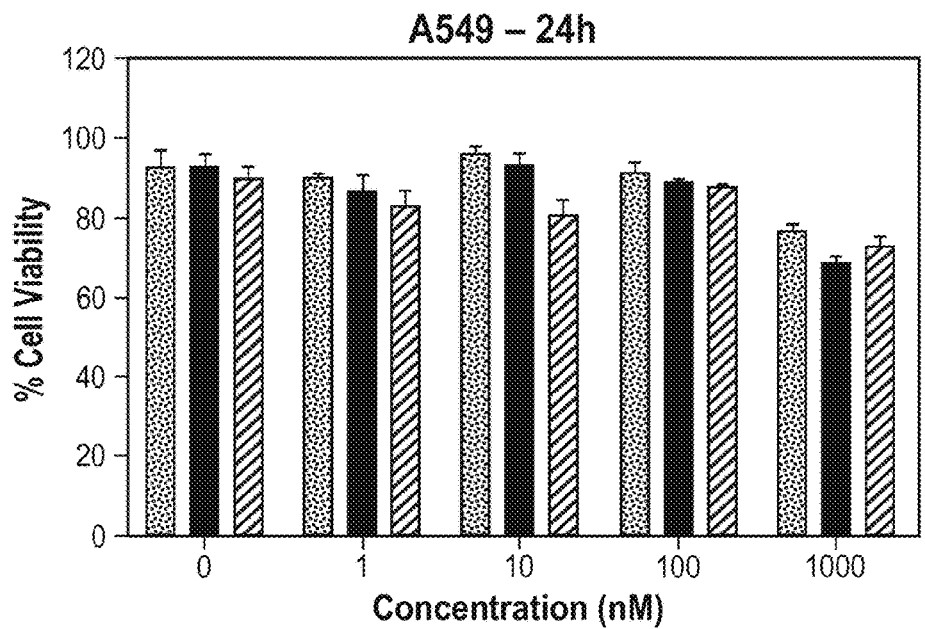

Cytotoxicity studies were performed to investigate whether the nanocarriers have inherent toxicity over the dose range used for the experiments performed. See FIGS. 3D and 3E. There was no apparent toxicity observed for the polymers at the tested dose range of 0-1 µM for 24 h with two tested cell lines, C166 and A-549. FIGS. 3D and 3E.

Example 11. Micelles Properties—Critical Micelles Concentrations (CMC)

The CMC was determined by the pyrene method, as commonly known in the art. Briefly, 0.5 mg of pyrene crystals in chloroform were added to each tube. The solvent was evaporated with nitrogen and product freeze-dried. Each tube containing pyrene crystals was shaken with polymers and polymer micelles at a concentration range of 0-0.8 mM in darkness for 24 h at room temperature. The following day, the unincorporated pyrene was filtered through 0.2 mm syringe filters. The filtrate was transferred to a 96-well plate as 100 mL in triplicates and the fluorescence intensity was measured with a multidetection microplate reader (Biotek, Winooski, Vt.) using 339/390 ex/emwavelengths.

Determination of critical micelle concentration (CMC) confirmed the potential of the developed polymeric systems for a drug delivery application. See FIG. 4A. The CMC of the polymers was compared to that of stable $PEG_{2K}$-PE micelles that demonstrated the CMC value of $2.5 \times 10^{-5}$ M. Mixed micellar system (MDM) and the polymeric dendrimer (MD) had CMC values of $5 \times 10^{-5}$ M and approximately $10 \times 10^{-5}$ M, respectively. The synthesized polymer MD, mixed with PEG-PE (MDM), can form a stable mixed micellar system with a low CMC, but failed to efficiently self-assemble alone in the system, resulting in a very slow rise in the solution fluorescence. G(4)-D showed no pyrene incorporation.

Dox-loading efficiency of the nanocarriers was dependent on the CMC. The $PEG_{2K}$-PE had the lowest CMC value and the Dox-loading efficiency was ca. 65%. See FIG. 4B. The MDM's loading efficiency was ca. 42% and MD had the lowest loading efficiency (ca. 20%).

Example 12. Association with Cells

Flow cytometry analysis and visualization with confocal microcopy were performed to quantify the association of FITC-labeled nanocarriers with the cells. Confocal microscopy images showed significantly higher cellular accumulation of MD and MDM after 1 h incubation compared to G(4)-D, (FIG. 5A) with MD showing a higher cellular association than MDM. However, no significant difference in cell association was observed between the samples after 4 h. A time-dependent increase in the cellular association of nanocarriers was observed using FACS analysis. See FIG. 5B. The analysis of the internalization of nanocarriers was performed by quenching the surface-associated FITC-fluorescence with Trypan blue. See FIG. 5C. The data showed decreased fluorescence after the Trypan blue treatment, indicating that a higher portion of the cell-associated fluorescence was from surface association. However, it has been observed that the cellular internalization also significantly increases over time.

Example 13. Cellular Internalization

To assess the cellular internalization, Z-stacked images of the cells in the XY plane were obtained allowing different regions of the cells to be viewed along the Z-axis. See FIG. 5D. The center Z-slices out of 12 slices of uniform thickness showed that the FITC-labeled MD and MDM had significantly higher cellular internalization compared to parent G(4)-D.

Example 14. siRNA Delivery

The ability of the nanocarriers to deliver Cy-3-labeled GAPDH siRNA was investigated by FACS analysis. See FIG. 6A. There was a time-dependent increase in siRNA delivery observed within 2 h. Both MD and MDM delivered significantly higher amounts of siRNA than parent G(4)-D (geo mean of fluorescence. 3.56+/−0.06 for G(4)-D, 8.94+/−0.33 for MD, 6.68+/−0.22 for MDM and 3.39+/−0.37 for free siRNA), resulting in higher labeling of the cells with Cy-3-siRNA. Histogram and quadrant statistics (FIGS. 6B and 6C) showed that the MD-siRNA complex had a significantly higher cellular uptake than the MDM-siRNA complex. Quadrant statistics demonstrated that the G(4)-D-Cy3-siRNA complex shifted 7% of the total cell population to the lower right quadrant, whereas for the MD and MDM-Cy3-siRNA complexes, the cell population increased to 59.7 and 43.5%, respectively. Compared to free siRNA treatment, G(4)-D showed no improvement in siRNA delivery. Visualization of Cy3-siRNA:D, MD and MDM complex-dosed A549 cells supported the results of the FACS analysis that MD delivered higher amount of siRNA compared to G(4)-D and micellar dendrimer, MDM. However, both MD and MDM showed comparable siRNA-delivery efficiency compared to G(4)-D. See FIG. 6D.

Example 15. siRNA-Mediated Gene Silencing

Figure 7B:
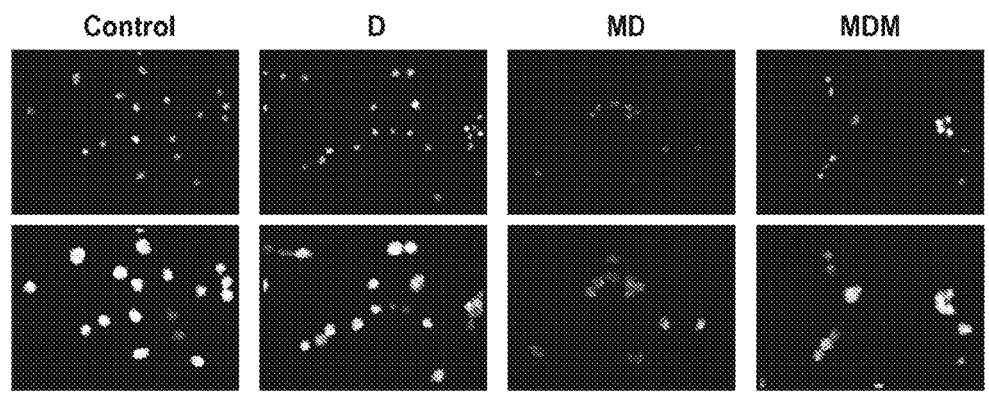

In vitro gene silencing of dendrimer-based siRNA-complexes was investigated using GFP-specific siRNA (siGFP) and non-specific siRNA (siNegative) in C166 cells-stably expressing GFP. The gene silencing efficacy was ca. 10% for the G(4)-D, ca. 22% for MD and 18% for MDM. See FIG. 7A. High GFP expression down-regulation was not observed with any dendriplexes. However, silencing efficacy was significantly higher for the modified dendrimer systems, MD and MDM compared to G(4)-D. The fluorescence microscopic visualization of the C166-GFP cells indicated that the siGFP, delivered by MD and MDM systems, had decreased GFP expression. FIG. 7B.

Example 16. Dox-Loading Efficiency, Drug Delivery and Cytotoxicity

Cytotoxicity of the dendrimers and modified dendrimers were determined with a CellTiter 96 Aqueous One Solution Cell Proliferation Assay kit following the manufacturer's protocol. C166-GFP and A549 cells were seeded in 96-well tissue culture plates at $5 \times 10^3$/well. The next day, the cells were incubated with G(4)-D, MD and MDM at varying concentrations (0-1000 nM) for 24 h. At the end of the incubation period, the cells were washed with PBS and supplemented with 100 mL of the serum free DMEM followed by the addition of 20 mL of Cell Titer Blue Assay Reagent. The cells were incubated with the reagent for 2 h. The fluorescence intensity was measured with a multi-detection microplate reader (Biotek, Winooski, Vt.) using 530/590 ex/em wavelengths. Cells treated with medium only were considered 100% viable.

For assessment of the Dox-loading efficiency, a calibration curve was plotted by measuring the fluorescence intensities of Dox over a concentration range of 0-30 mg/mL using a fluorescence microplate reader. An aliquot of Dox-loaded nanocarriers was diluted 100 times in water containing 1% Triton-X. The loading was determined as follows. The % of Dox loading polymers ¼ (Dox concentration in Dox-loaded nanocarriers obtained from the calibration curve)×100/Theoretical Dox concentration considering no loss during the Dox loading procedure.

Figure 8A:
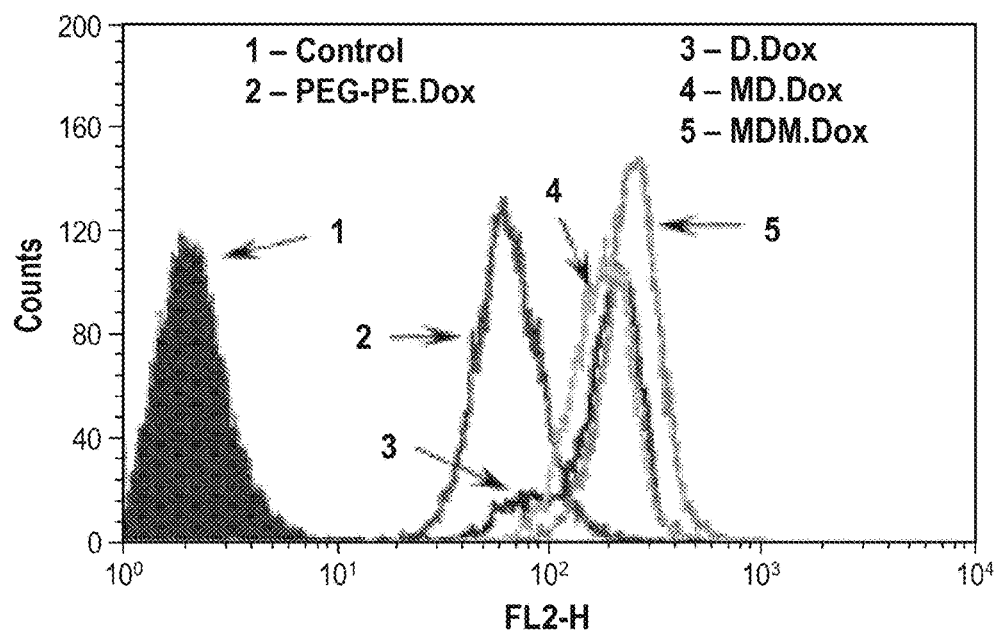
Figure 8B:
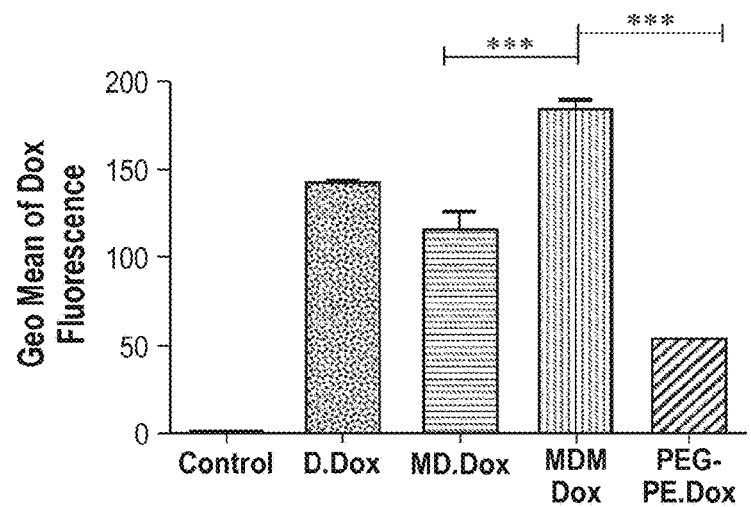

Apart from the ability of the nanocarrier systems to deliver siRNA, drug delivery efficiency of the nanocarriers was also investigated. See FIG. 8A. The ability of the nanocarriers to deliver a fixed Dox dose of 4 mg/mL, irrespective of their loading was assessed by FACS analysis. FIG. 8A. It was observed that the MDM delivered a higher amount of Dox to the cells (geo mean of cellular fluorescence. 184.7+/−4.4) than D (142.3+/−1.0), MD (116.1+/−9.3) and PEG-PE (54.9+/−0.04). See FIG. 8B.

Example 17. siRNA/Drug Co-Delivery

Figure 9A:
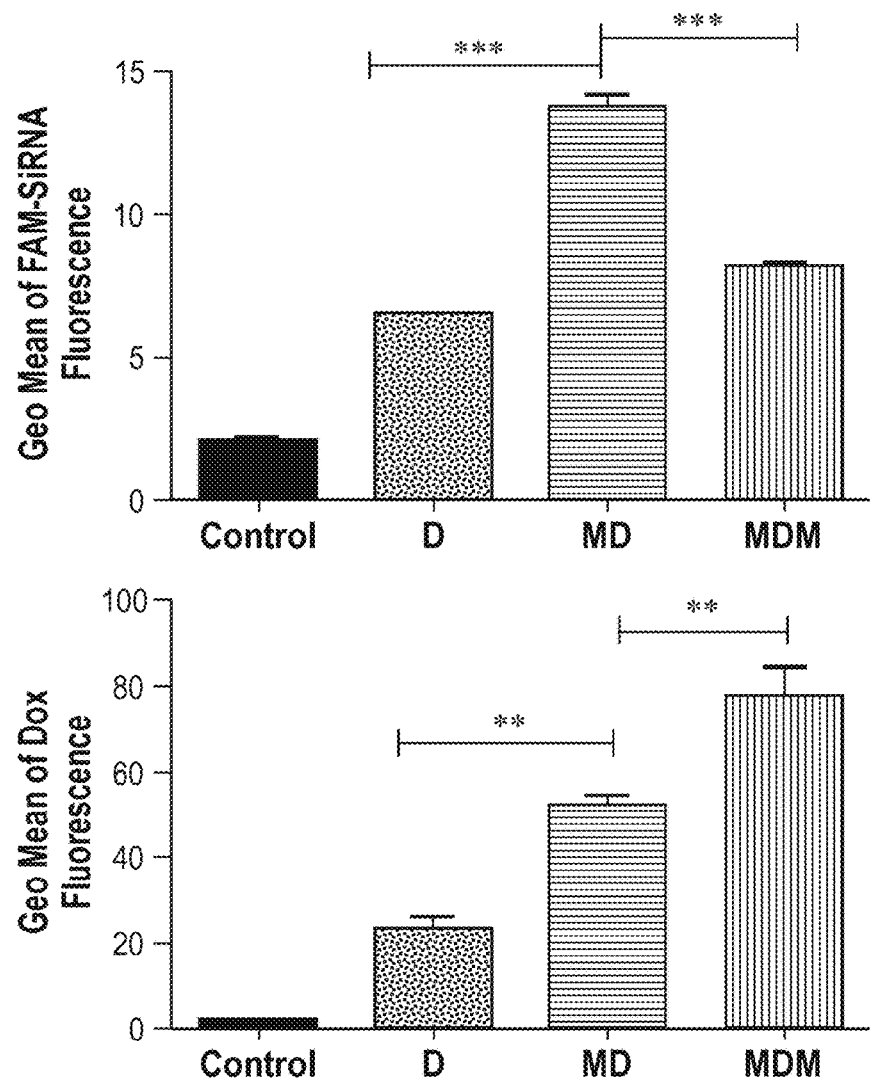
Figure 9B:
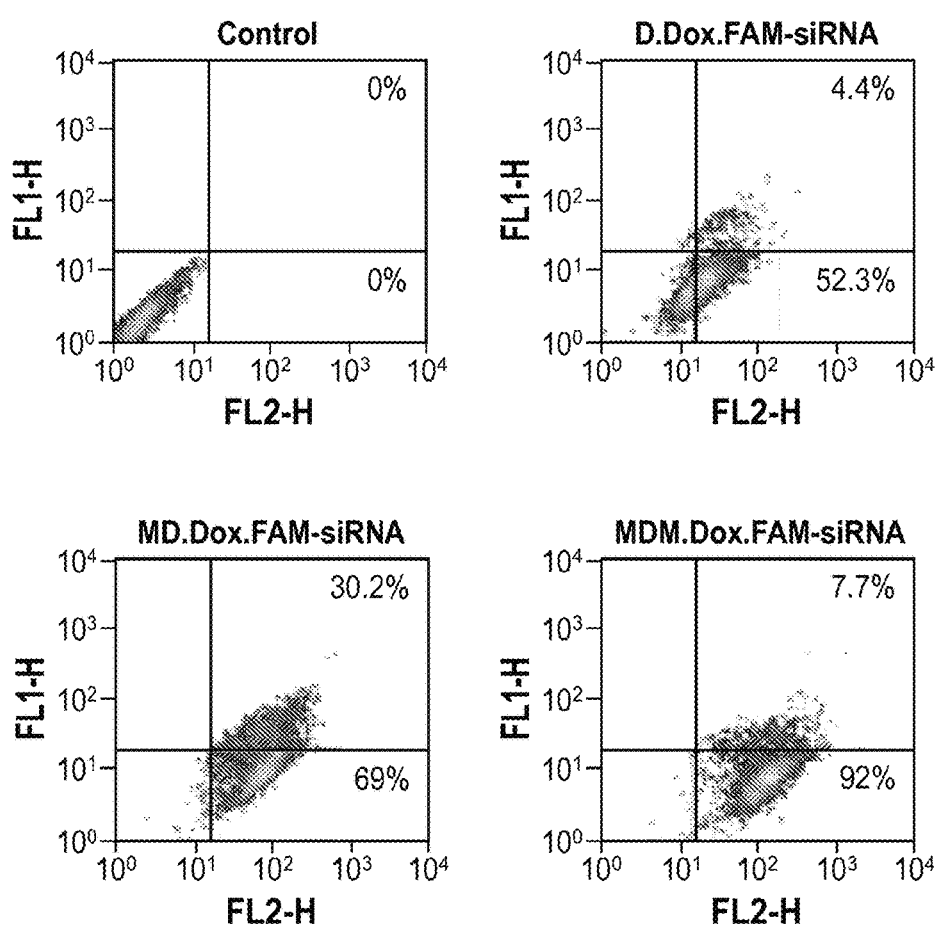

For the purpose of drug-siRNA co-delivery, Dox-loaded nanocarriers were complexed with FAM-labeled siRNA. Simultaneous labeling of cells with green and red fluorescence due to the co-delivery of FAM-siRNA and Dox was analyzed by flow cytometry. FIG. 9A. Higher labeling of cell population was observed with FAM-siRNA in the MD:Dox:siRNA complex (Geo mean of fluorescence. 13.7+/−0.3) than the D:Dox:siRNA (6.5+/−0.0) and MDM:Dox:siRNA (8.3+/−0.1) complex-treated cell populations, whereas higher Dox-labeling of cells was observed with MDM:Dox:siRNA (77.3+/−4.9) than with the other nanocarriers (22.4+/−2.2 for D:Dox:siRNA and 52.4+/−1.6 for MD:Dox:siRNA). The representative quadrant statistics (FIG. 9B) showed the shift in the cell population due to increased labeling with the nanocarriers in both FL1 and FL2 axis. Shift of the cell population in upper right quadrant, indicative of siRNA labeling was highest in MD (30.2% compared to 4.4% for D and 7.7% for MDM), whereas in lower right quadrant, indicative of Dox labeling was highest in MDM (92% compared to 52.3 for D and 69% for MD).

Example 18. Serum Stability

Serum stability of naked siRNA and siRNA complexed with MD and MDM were investigated by incubating the siRNA-dendrimer complexes in 50% FBS at 37° C. Eight samples were prepared by mixing 750 ng of siRNA and polymers at an N/P ratio of 10 in RNAse-free water and incubated for 20 min. Equal volumes of FBS were added and the solutions were incubated for 1 h, 6 h and 24 h. In samples, without both FBS and naked siRNA, water was added to make up the volume. The complex was dissociated by addition of heparin sulfate (10 units/mg of siRNA) and analyzed by gel electrophoresis using 0.8% agarose gel containing EtBr.

To check on whether the prepared nanocarriers are suitable for in vivo application, the serum stability of the siRNA in dendriplexes was assessed. The result showed that the free siRNA showed partial instability at 1 h and complete enzymatic digestion within 6 h, whereas the siRNA, complexed with dendrimers, showed complete protection against enzymatic degradation.

While certain embodiments have been illustrated and described, it should be understood that changes and modifications can be made therein in accordance with ordinary skill in the art without departing from the technology in its broader aspects as defined in the following claims.

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A co-polymer of formula (I)

A-B-C-D       (I)

or a pharmaceutically acceptable salt thereof, wherein
   A is a poly(amidoamine) dendrimer (PAMAM);
   B is selected from the group consisting of a bond, —CO—, —COO—, —CONR$_5$—, —CH$_2$CH$_2$CO—, —CH$_2$CH$_2$COO—, —CH$_2$CH$_2$CONR$_5$—, —SO$_2$— and —SO$_2$NR$_5$—;
   C is —(R$_4$O)$_n$—;
   D is F, EF or E(F)$_2$;
   E is selected from the group consisting of a bond, —COO—, —CONR$_5$—, —CH$_2$CH$_2$COO—, —CH$_2$CH$_2$CONR$_5$—, —SO$_2$NR$_5$—;

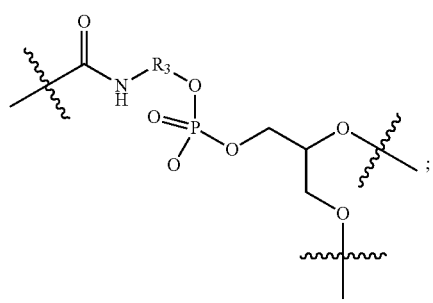

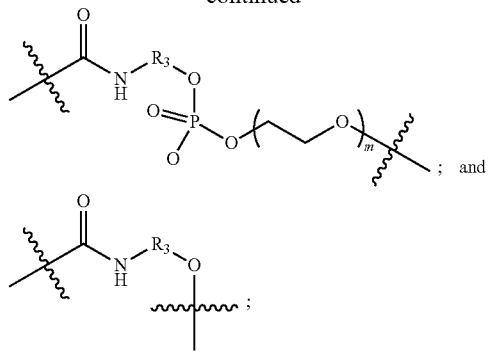

F is —CO—C$_6$-C$_{22}$-alkyl or —CO—C$_6$-C$_{22}$-alkenyl;
R$_3$ is C$_2$-C$_8$ alkylene, optionally substituted;
R$_4$ is C$_2$-C$_8$ alkylene, optionally substituted;
R$_5$ is hydrogen or C$_1$-C$_6$ alkyl, optionally substituted;
n is from 1 to 50; and
m is from 1 to 50.

2. The co-polymer of claim 1, wherein A is G(4)-PAMAM.
3. The co-polymer of claim 1, wherein B is —CO—.
4. The co-polymer of claim 1, wherein n is from 1 to 20.
5. The co-polymer of claim 1, wherein D is E(F)$_2$ and E comprises sn-glycero-3-phosphoethanolamine.
6. The co-polymer of claim 1, wherein D comprises a dioleoylphosphatidyl ethanolamine (DOPE) moiety.
7. The co-polymer of claim 1, wherein E comprises polyethylene glycol-dioleolphosphatidylethanolamine.
8. The co-polymer of claim 1, wherein F is oleoyl.
9. A micellar composition comprising a co-polymer, wherein the co-polymer comprises formula (I)

A-B-C-D       (I)

or a pharmaceutically acceptable salt thereof, wherein
   A is a poly(amidoamine) dendrimer (PAMAM);
   B is selected from the group consisting of a bond, —CO—, —COO—, —CONR$_5$—, —CH$_2$CH$_2$CO—, —CH$_2$CH$_2$COO—, —CH$_2$CH$_2$CONR$_5$—, —SO$_2$— and —SO$_2$NR$_5$—;
   C is —(R$_4$O)$_n$—;
   D is F, EF or E(F)$_2$;
   E is selected from the group consisting of a bond, —COO—, —CONR$_5$—, —CH$_2$CH$_2$COO—, —CH$_2$CH$_2$CONR$_5$—, —SO$_2$NR$_5$—;

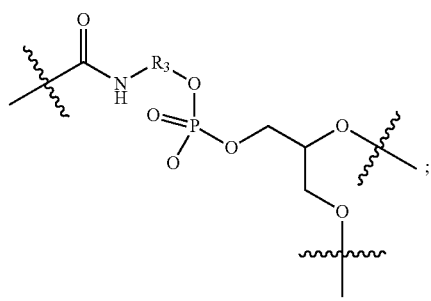

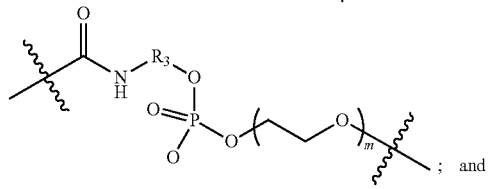

-continued

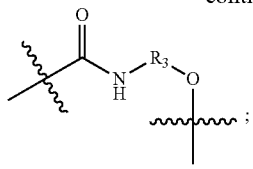

F is —CO—C$_6$-C$_{22}$-alkyl or —CO—C$_6$-C$_{22}$-alkenyl;
R$_3$ is C$_2$-C$_8$ alkylene, optionally substituted;
R$_4$ is C$_2$-C$_8$ alkylene, optionally substituted;
R$_5$ is hydrogen or C$_1$-C$_6$ alkyl, optionally substituted;
n is from 1 to 50; and
m is from 1 to 50.

10. The micellar composition of claim 9, further comprising an additional co-polymer.

11. The micellar composition of claim 10, wherein the additional co-polymer is PEG-$_{5K}$-PE.

12. The micellar composition of claim 10, wherein the co-polymer and the additional co-polymer are in a ratio of from about 1:0.1 to about 1:10.

13. The micellar composition of claim 10, wherein the co-polymer and the additional co-polymer are in a ratio of about 1:1.

14. The micellar composition of claim 9, further comprising siRNA.

15. The micellar composition of claim 14, further comprising a small-molecule drug.

16. The micellar composition of claim 15, wherein the small-molecule drug is a chemotherapeutic drug.

17. The micellar composition of claim 16, wherein the chemotherapeutic drug is doxorubicin.

18. A method for delivering siRNA and an antineoplastic drug into one or more cells of a subject comprising administering to the subject an effective amount of a composition comprising a co-polymer of claim 1, siRNA and a chemotherapeutic drug.

19. The method of claim 18, wherein the co-polymer of claim 1, siRNA and chemotherapeutic drug have a ratio of about (10-1,000):1:(10-1,000).

20. The method of claim 18, wherein the chemotherapeutic drug is doxorubicin.

* * * * *